(12) United States Patent
Ootsuki

(10) Patent No.: US 10,844,283 B2
(45) Date of Patent: Nov. 24, 2020

(54) POLYMERIZABLE LIQUID CRYSTAL COMPOUND, POLYMERIZABLE LIQUID CRYSTAL COMPOSITION AND LIQUID CRYSTAL POLYMERIZED FILM

(71) Applicants: JNC CORPORATION, Tokyo (JP); JNC PETROCHEMICAL CORPORATION, Tokyo (JP)

(72) Inventor: Daisuke Ootsuki, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 150 days.

(21) Appl. No.: 15/896,019

(22) Filed: Feb. 13, 2018

(65) Prior Publication Data

US 2018/0244998 A1      Aug. 30, 2018

(30) Foreign Application Priority Data

Feb. 17, 2017   (JP) .................................. 2017-027614

(51) Int. Cl.
*C09K 19/38*   (2006.01)
*C07C 69/757*  (2006.01)
(Continued)

(52) U.S. Cl.
CPC ........ *C09K 19/3861* (2013.01); *C07C 69/757* (2013.01); *C07C 69/78* (2013.01);
(Continued)

(58) Field of Classification Search
None
See application file for complete search history.

(56) References Cited

U.S. PATENT DOCUMENTS

| 5,569,640 | A | 10/1996 | Rheinheimer et al. |
| 5,777,118 | A * | 7/1998 | Rheinheimer ....... C07D 239/60 544/318 |
| 2010/0304148 | A1 | 12/2010 | Hirai et al. |

FOREIGN PATENT DOCUMENTS

| JP | H07186219 | 7/1995 |
| JP | H08505168 | 6/1996 |

(Continued)

OTHER PUBLICATIONS

Aws M. Hamdy et al., "Regioselective Suzuki-Miyaura reactions of 4,7-dichloro-N-methylisatin. Synthesis, anti-HIV activity and modeling study", RSC Advances, Dec. 2015, pp. 107360-107369.

(Continued)

*Primary Examiner* — Cynthia H Kelly
*Assistant Examiner* — Anna Malloy
(74) *Attorney, Agent, or Firm* — JCIPRNET

(57) ABSTRACT

A polymerizable liquid crystal compound represented by formula (1). In formula (1), $A^1$ is 1,4-phenylene, 1,4-cyclohexylene, 1,4-cyclohexenylene, pyridine-2,5-diyl, 1,3-dioxane-2,5-diyl or naphthalene-2,6-diyl, $Z^1$ is a connecting group, m and n are independently an integer from 0 to 5, in which an expression: $1 \leq m+n \leq 8$ holds, $X^1$ is alkylene having 1 to 5 carbons, in which an atom thereof may be replaced by a hetero atom, and at least one of $R^1$ is a polymerizable functional group.

(Continued)

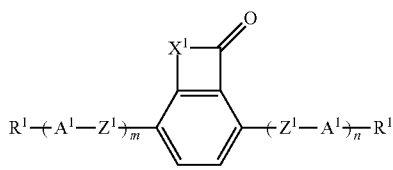

15 Claims, 1 Drawing Sheet

(51) Int. Cl.
*C07C 69/92* (2006.01)
*C07C 69/78* (2006.01)
*C08F 22/20* (2006.01)
*G02B 5/30* (2006.01)
*C09K 19/04* (2006.01)

(52) U.S. Cl.
CPC .............. *C07C 69/92* (2013.01); *C08F 22/20* (2013.01); *G02B 5/3016* (2013.01); *C09K 2019/0448* (2013.01)

(56) References Cited

FOREIGN PATENT DOCUMENTS

| | | |
|---|---|---|
| JP | 2007-148098 | 6/2007 |
| JP | 2008525498 | 7/2008 |
| JP | 2009-184974 | 8/2009 |
| JP | 2010-241791 | 10/2010 |
| WO | 9415258 | 7/1994 |
| WO | 2006071940 | 7/2006 |
| WO | 2015134039 | 9/2015 |

OTHER PUBLICATIONS

Colin O. Hayes et al., "Effect of Ring Functionalization on the Reaction Temperature of Benzocyclobutene Thermoset Polymers", Macromolecules, May 5, 2016, pp. 3706-3715.

\* cited by examiner

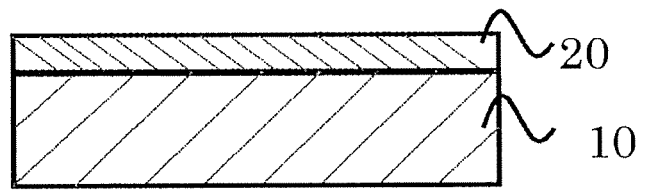

POLYMERIZABLE LIQUID CRYSTAL COMPOUND, POLYMERIZABLE LIQUID CRYSTAL COMPOSITION AND LIQUID CRYSTAL POLYMERIZED FILM

CROSS-REFERENCE TO RELATED APPLICATIONS

This application claims the priority benefit of Japanese application serial no. 2017-027614, filed on Feb. 17, 2017. The entirety of the above-mentioned patent application is hereby incorporated by reference herein and made a part of this specification.

TECHNICAL FIELD

The invention relates to a polymerizable liquid crystal compound, a liquid crystal composition containing the polymerizable liquid crystal compound, a liquid crystal polymerized film prepared by applying the liquid crystal composition as a raw material, and a product containing the liquid crystal polymerized film.

BACKGROUND ART

A liquid crystal polymerized film prepared by applying a polymerizable liquid crystal composition as a raw material and polymerizing the composition serves as a material of a phase difference film, an optical compensation film, a reflection film, a selective reflection film, an antireflection film, a viewing angle compensation film, a liquid crystal alignment film, a polarizing device, a circularly polarizing device, an elliptically polarizing device and other polarizing plates. Moreover, such a liquid crystal polymerized film can be utilized as a material of a display device for the purpose of achieving high definition of image display of a liquid crystal display device, an organic electroluminescence display and any other display device.

A stretched polymer film has birefringence, and therefore has been used as the phase difference film. The phase difference film using the liquid crystal polymerized film is further easily prepared than the stretched polymer film. In the phase difference film using the liquid crystal polymerized film, birefringence is further easily controlled in comparison with the stretched polymer film. The phase difference film using the liquid crystal polymerized film can be further thinned than the stretched polymer film. The phase difference film using the liquid crystal polymerized film is further durable than the stretched polymer film.

According to Patent literature No. 1, a liquid crystal polymerized film is formed by applying, to a substrate, a polymerizable liquid crystal composition solution prepared by dissolving a polymerizable liquid crystal composition in a solvent, aligning liquid crystal molecules, and applying polymerization treatment thereto by irradiation with ultraviolet light.

Patent literature No. 2 discloses utilization of a polymerizable liquid crystal compound having an alkyl group having at least 5 carbons in a lateral position of a benzene ring as a component of a polymerizable liquid crystal composition.

Patent literature No. 3 discloses utilization of a polymerizable liquid crystal compound having a norbornane skeleton as a component of a polymerizable liquid crystal composition.

In the polymerizable liquid crystal composition containing the polymerizable liquid crystal compound in which a bulky group is introduced into the lateral position of a phenylene structure, a liquid-crystal-phase's lifetime is long upon preparing a liquid crystal polymer. Therefore, in the polymerizable liquid crystal composition containing such a polymerizable liquid crystal compound, the liquid crystal polymerized film is simply produced. However, the polymerizable liquid crystal composition containing such a polymerizable liquid crystal compound has features in which (a) a maximum temperature of the liquid crystal phase is low, or the liquid crystal phase itself is lost, and (b) birefringence is low. Development of a polymerizable liquid crystal composition having a long liquid-crystal-phase's lifetime, a not low maximum temperature, and not low birefringence has been difficult.

CITATION LIST

Patent Literature

Patent literature No. 1: JP 2007-148098 A.
Patent literature No. 2: JP 2009-184974 A.
Patent literature No. 3: JP 2010-241791 A.

SUMMARY OF INVENTION

Technical Problem

The technical problem is to develop a polymerizable liquid crystal compound serving as a component of a raw material of a liquid crystal polymerized film, thereby easily producing the liquid crystal polymerized film, in which alignment defects of the liquid crystal polymerized film are eliminated, and the liquid crystal polymerized film can be thinned while production cost is suppressed. An objective of the invention is to reduce defects of an optical function of a product produced by applying such a liquid crystal polymerized film as a material to thin the product while material cost of the product is suppressed.

Solution to Problem

A first aspect of the invention is a polymerizable liquid crystal compound, represented by formula (1):

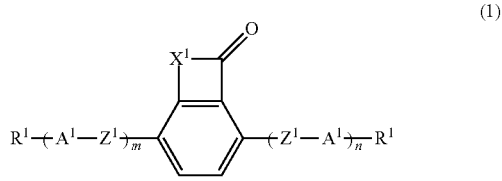

wherein, in formula (1), $A^1$ is independently 1,4-phenylene, 1,4-cyclohexylene, 1,4-cyclohexenylene, pyridine-2,5-diyl, 1,3-dioxane-2,5-diyl or naphthalene-2,6-diyl, and in the 1,4-phenylene or naphthalene-2,6-diyl, at least one hydrogen may be replaced by fluorine, chlorine, trifluoromethyl, alkyl having 1 to 10 carbons, alkenyl having 2 to 10 carbons, alkoxy having 1 to 10 carbons, alkoxycarbonyl having 1 to 10 carbons, alkylester having 1 to 10 carbons, alkanoyl having 1 to 10 carbons or a polymerizable functional group, $Z^1$ is independently a single bond, —OCH$_2$—, —CH$_2$O—, —COO—, —OCO—, —CF$_2$O—, —OCF$_2$—, —CH$_2$CH$_2$—, —CF$_2$CF$_2$—, —OCH$_2$CH$_2$O—, —CH=CHCOO—, —OCOCH=CH—, —CH$_2$CH$_2$COO—, —OCOCH$_2$CH$_2$—, —CH₂CH₂OCO—, —COOCH₂CH₂—, —CH=CH—, —N=CH—, —CH=N—, —N=C(CH₃)—, —C(CH₃)=N—, —N=N—, —C≡C— or —CH=N—N=CH—, m and n are independently an integer from 0 to 5, in which an expression: 1≤m+n≤8 holds, $X^1$ is alkylene having 1 to 5 carbons, and in the alkylene, at least one piece of —CH₂— may be replaced by —CO—, —S—, —O— or —NH—, at least one piece of —CH₂CH₂— may be replaced by —CH=CH—, and at least one hydrogen in —CH₂—, —CH= or —NH— described above may be replaced by fluorine, chlorine, trifluoromethyl, alkyl having 1 to 10 carbons or alkanoyl having 1 to 10 carbons, one of $R^1$ is a polymerizable functional group, and the other of $R^1$ is a polymerizable functional group, hydrogen, fluorine, chlorine, trifluoromethyl, trifluoromethoxy, cyano, alkyl having 1 to 12 carbons, alkoxy having 1 to 12 carbons, alkenyl having 2 to 12 carbons, alkylester having 1 to 12 carbons or alkoxycarbonyl having 1 to 12 carbons.

A second aspect of the invention is the polymerizable liquid crystal compound according to the first aspect, wherein the polymerizable functional group is independently represented by formula (2):

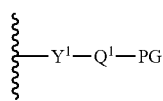

(2)

wherein, in formula (2), $Y^1$ is a single bond, —O—, —COO—, —OCO— or —OCOO—, and $Q^1$ is a single bond or alkylene having 1 to 20 carbons, and in the alkylene, at least one piece of —CH₂— may be replaced by —O—, —COO— or —OCO—, and PG is a polymerizable group represented by any one of formula (PG-1) to formula (PG-9):

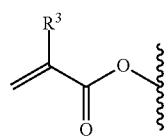

(PG-1)

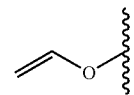

(PG-2)

(PG-3)

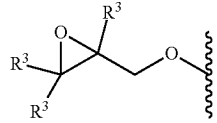

(PG-4)

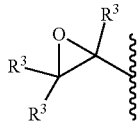

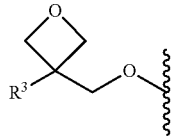

(PG-5)

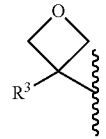

(PG-6)

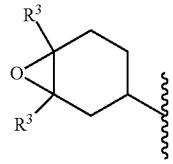

(PG-7)

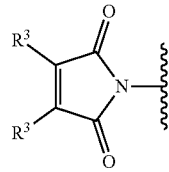

(PG-8)

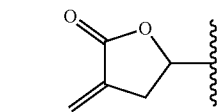

(PG-9)

wherein, in formula (PG-1) to formula (PG-9), $R^3$ is each independently hydrogen, fluorine, methyl, ethyl or trifluoromethyl.

A third aspect of the invention is the polymerizable liquid crystal compound according to the first or second aspect, wherein $Z^1$ is independently a single bond, —OCH₂—, —CH₂O—, —COO—, —OCO—, —CH₂CH₂—, —CH=CHCOO—, —OCOCH=CH—, —CH₂CH₂COO— or —OCOCH₂CH₂—.

A fourth aspect of the invention is the polymerizable liquid crystal compound according to the second aspect, wherein both of $R^1$ are a group represented by formula (2).

A fifth aspect of the invention is the polymerizable liquid crystal compound according to any one of the first to fourth aspects, wherein $X^1$ is alkylene having 2 to 4 carbons, and in the alkylene, —CH₂— may be replaced by —CO—, —S—, —O— or —NH—, and at least one hydrogen may be replaced by fluorine, chlorine, trifluoromethyl, alkyl having 1 to 5 carbons or alkanoyl having 1 to 5 carbons.

A sixth aspect of the invention is the polymerizable liquid crystal compound according to any one of the second to fifth aspects, wherein both of $R^1$ are a group represented by formula (2), and PG is a polymerizable group represented by formula (PG-1).

A seventh aspect of the invention is the polymerizable liquid crystal compound according to any one of the first to sixth aspects, wherein m and n are independently 1, 2 or 3.

An eighth aspect of the invention is a polymerizable liquid crystal composition, containing the polymerizable liquid crystal compound according to any one of the first to seventh aspects.

A ninth aspect of the invention is a polymerizable liquid crystal composition, containing 10 to 100% by weight of the polymerizable liquid crystal compound according to any one of the first to seventh aspects, based on the total weight of the polymerizable liquid crystal compound.

A tenth aspect of the invention is a liquid crystal polymerized film, prepared by polymerizing the polymerizable liquid crystal composition according to the eighth or ninth aspect.

An eleventh aspect of the invention is a liquid crystal polymerized film composed of a substrate-embedded liquid crystal polymer, and liquid crystal polymerized film having an alignment film on a substrate, wherein a polymerizable liquid crystal compound in the polymerizable liquid crystal composition according to the eighth or ninth aspect is aligned by the alignment film and polymerized.

A twelfth aspect of the invention is the liquid crystal polymerized film according to the eleventh aspect, wherein the liquid crystal compound in the polymerizable liquid crystal composition is immobilized in a state of homogeneous alignment.

A thirteenth aspect of the invention is a phase difference film formed of the liquid crystal polymerized film according to any one of the tenth to twelfth aspects.

A fourteenth aspect of the invention is a polarizing plate having the liquid crystal polymerized film according to any one of the tenth to twelfth aspects.

A fifteenth aspect of the invention is a display device having the liquid crystal polymerized film according to any one of the tenth to twelfth aspects.

Advantageous Effects of Invention

The present inventors have completed the invention by finding the followings:

(1) with regard to a polymerizable liquid crystal compound according to first to seventh aspects of the invention, a liquid crystal polymerized film is easily produced by applying the polymerizable liquid crystal compound according to the first to seventh aspects of the invention as a component of a liquid crystal composition being a raw material of a liquid crystal polymer;

(2) the liquid crystal polymerized film is easily produced by applying a polymerizable liquid crystal composition according to eighth and ninth aspects of the invention as the raw material;

(3) with regard to a liquid crystal polymerized film according to tenth to twelfth aspects of the invention, which is prepared by applying the polymerizable liquid crystal composition according to the eighth and ninth aspects of the invention as the raw material has no alignment defects, and can be thinned while production cost is suppressed; and (4) defects of an optical function of a material according to thirteenth to fifteenth aspects of the invention, the aspects having the liquid crystal polymerized film according to the tenth to twelfth aspects of the invention, can be reduced, production cost of the material can be decreased, and various products can be thinned.

BRIEF DESCRIPTION OF DRAWING

The diagram shows one example of a substrate-embedded liquid crystal polymer.

DESCRIPTION OF EMBODIMENTS

In the invention, "liquid-crystal-phase's lifetime" means a time from a time at which, on a substrate in contact with a hot plate at 80° C., the substrate on which a polymerizable liquid crystal composition is applied is moved to an atmosphere at room temperature to a time at which a crystal is precipitated from the polymerizable liquid crystal composition. The liquid-crystal-phase's lifetime serves as a reference value of the time during which a liquid crystal polymer can be prepared by polymerization while alignment of liquid crystals of the polymerizable liquid crystal composition is maintained. The liquid crystal polymer without alignment defects is further easily prepared as the liquid-crystal-phase's lifetime is longer.

In the invention, "compound (X)" means a compound represented by formula (X). Here, an alphabet X in "compound (X)" is a character string, a numerical character, a symbol or the like.

In the invention, "liquid crystal composition" means a mixture having a liquid crystal phase.

In the invention, "liquid crystal compound" is a generic term for (A) a compound having a liquid crystal phase as a pure substance, and (B) a compound serving as a component of the liquid crystal composition.

In the invention, "polymerizable functional group" means a functional group that is polymerized by a means such as light, heat and a catalyst, if a compound has the group therein, to change the compound into a polymer having larger molecular weight.

In the invention, "monofunctional compound" means a compound having one polymerizable functional group.

In the invention, "polyfunctional compound" means a compound having a plurality of polymerizable functional groups.

In the invention, "X-functional compound" means a compound having X pieces of polymerizable functional groups, in which an alphabet X in "X functional compound" is an integer.

In the invention, "polymerizable compound" means a compound having at least one polymerizable functional group.

In the invention, "polymerizable liquid crystal compound" means a polymerizable compound being a liquid crystal compound.

In the invention, "non-liquid crystal polymerizable compound" means a polymerizable compound being a compound having no liquid crystal phase in the pure substance.

In the invention, "polymerizable liquid crystal composition" means a composition containing a polymerizable compound and a liquid crystal compound, and a composition containing "polymerizable liquid crystal compound."

In the invention, "polymerizable liquid crystal composition solution" means a material containing a polymerizable liquid crystal composition and a solvent.

In the invention, "liquid crystal polymer" means a portion obtained by polymerizing a polymerizable liquid crystal composition.

In the invention, "substrate-embedded liquid crystal polymer" means a material that is obtained by polymerizing a polymerizable liquid crystal composition on a substrate and contains the substrate.

In the invention, "highly functional polarizing plate" means a substrate-embedded liquid crystal polymer prepared by applying a polarizing plate as a substrate.

In the drawing, a reference numeral 20 is a liquid crystal polymer. In the drawing, a reference numeral 10 is a substrate.

In the invention, "liquid crystal polymerized film" is a generic term for a liquid crystal polymer and a substrate-embedded liquid crystal polymer, and should include not only a film-shaped material but also a plate-shaped material.

In the invention, "phase difference film" means a device having optical anisotropy, and in the form of a film or plate-shaped material.

In the invention, "polarizing plate" means a device that causes control of light transmission in a specific direction to prepare linearly polarized light, and in the form of a film or plate-shaped material.

In the invention, "tilt angle" means an angle between an alignment direction of liquid crystal molecules in a major axis, and a substrate surface.

In the invention, "homogeneous alignment" means an alignment state in which the tilt angle is from 0 degrees to 5 degrees.

In the invention, "homeotropic alignment" means an alignment state in which the tilt angle is from 85 degrees to 90 degrees.

In the invention, "twist alignment" means an alignment state in which an alignment direction of liquid crystal molecules in a major axis direction is in parallel to a substrate, and accordingly as the liquid crystal molecules are separated from the substrate, the liquid crystal molecules are twisted stepwise with a perpendicular to a substrate surface as an axis.

In the invention, "room temperature" means 15° C. to 35° C.

When the functional group described below is described in the chemical formula, a wavy line portion should mean a bonding position of the functional group. Here, C described below represents an arbitrary atom or functional portion.

The substrate-embedded liquid crystal polymer of the invention is prepared in the following steps:

(1) a material prepared by mixing a polymerizable liquid crystal composition containing a polymerizable liquid crystal compound in a solvent is applied onto a substrate;

(2) the solvent is eliminated from the material prepared by mixing the polymerizable liquid crystal composition on the substrate in the solvent to form a coating film of the polymerizable liquid crystal composition on the substrate according to warming or any other method; and (3) the polymerizable liquid crystal composition is polymerized by means of light, heat, a catalyst or the like in a state in which the polymerizable liquid crystal composition on the substrate is aligned to prepare the substrate-embedded liquid crystal polymer.

As a method of eliminating the liquid crystal polymer from the substrate-embedded liquid crystal polymer and fixing the polymer to another substrate, the following method is known:

(1) a substrate-embedded liquid crystal polymer is laminated with a substrate having an adhesive layer in such a manner that the liquid crystal polymer is brought into contact with the adhesive layer;

(2) a material laminated in such a manner that the liquid crystal polymer is brought into contact with the adhesive layer is peeled off in a place between a substrate portion of the substrate-embedded liquid crystal polymer, and the liquid crystal polymer; and (3) the liquid crystal polymer having the adhesive layer on the substrate is fixed to another substrate in a manner similar to the steps (1) and (2) described above.

1. Polymerizable Liquid Crystal Compound

In a polymerizable liquid crystal compound represented by compound (1), the temperature range in which the liquid crystal phase is formed in the range of 60° C. to 120° C. is wide, and a maximum temperature at which the liquid crystal phase is formed is high.

The polymerizable liquid crystal compound in which a temperature at which the liquid crystal phase is formed is 60° C. or higher can cause stabilization of the liquid crystal phase of the polymerizable liquid crystal composition containing the compound, and suppression of alignment defects of the polymerizable liquid crystal composition coated on the substrate.

The polymerizable liquid crystal compound in which the temperature at which the liquid crystal phase is fainted is 120° C. or lower can cause suppression of crystallization of the polymerizable liquid crystal composition containing the compound, and suppression of alignment defects of the polymerizable liquid crystal composition coated on the substrate. Formation of crystals from the polymerizable liquid crystal composition coated on the substrate causes alignment defects of the liquid crystal polymer.

The temperature range in which the liquid crystal phase is formed in the range of 60° C. to 120° C. is wide, and therefore if the polymerizable liquid crystal compound represented by compound (1) is applied as a component of the liquid crystal composition being the raw material of the liquid crystal polymer, the liquid crystal polymerized film is easily produced.

In the polymerizable liquid crystal compound represented by compound (1), the temperature range in which the liquid crystal phase is famed in the range of 60° C. to 120° C. is as wide as substantially 30 K to 60 K.

The polymerizable liquid crystal compound represented by compound (1) is easily dissolved in various solvents.

Upon producing the liquid crystal polymerized film by applying the liquid crystal composition as the raw material of the liquid crystal polymer, a step of applying a polymerizable liquid crystal composition solution exists. In the polymerizable liquid crystal compound easily dissolved in various solvents, restrictions on the solvent in production are small, and therefore the film is easily produced.

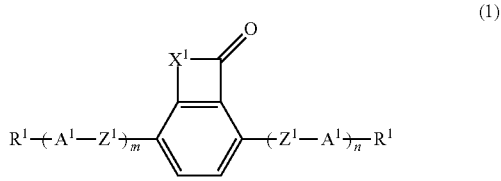

(1)

In formula (1), $A^1$ is independently 1,4-phenylene, 1,4-cyclohexylene, 1,4-cyclohexenylene, pyridine-2,5-diyl, 1,3-dioxane-2,5-diyl or naphthalene-2,6-diyl, and in the 1,4-phenylene or naphthalene-2,6-diyl, at least one hydrogen may be replaced by fluorine, chlorine, trifluoromethyl, alkyl having 1 to 10 carbons, alkoxy having 1 to 10 carbons, alkenyl having 2 to 10 carbons, alkoxycarbonyl having 1 to 10 carbons, alkylester having 1 to 10 carbons, alkanoyl having 1 to 10 carbons or a polymerizable functional group. Polymerization by light or heat is easy, and therefore the polymerizable functional group is preferably a group represented by formula (2).

Moreover, when $A^1$ is 1,4-phenylene or 1,4-cyclohexylene, the solubility in the organic solvent is high, and the temperature range of the liquid crystal phase is easily widened, and therefore such a case is further preferred.

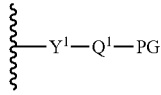
(2)

wherein, $Y^1$ is a single bond, —O—, —COO—, —OCO— or —OCOO—, and $Q^1$ is a single bond or alkylene having 1 to 20 carbons, and in the alkylene, at least one piece of —CH$_2$— may be replaced by —O—, —COO— or —OCO—, and PG is a functional group represented by any one of formula (PG-1) to formula (PG-9).

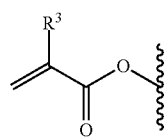
(PG-1)

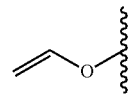
(PG-2)

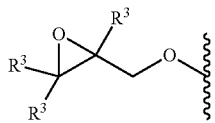
(PG-3)

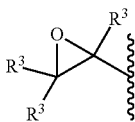
(PG-4)

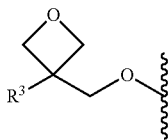
(PG-5)

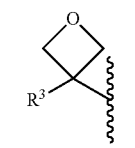
(PG-6)

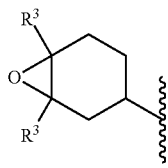
(PG-7)

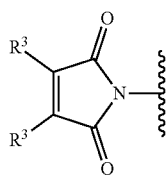
(PG-8)

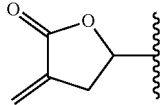
(PG-9)

wherein, in formula (PG-1) to formula (PG-9), $R^3$ is independently hydrogen, halogen, methyl, ethyl or trifluoromethyl.

$Z^1$ is independently a single bond, —OCH$_2$—, —CH$_2$O—, —COO—, —OCO—, —CF$_2$O—, —OCF$_2$—, —CH$_2$CH$_2$—, —CF$_2$CF$_2$—, —OCH$_2$CH$_2$O—, —CH=CHCOO—, —OCOCH=CH—, —CH$_2$CH$_2$COO—, —OCOCH$_2$CH$_2$—, —CH$_2$CH$_2$OCO—, —COOCH$_2$CH$_2$—, —CH=CH—, —N=CH—, —CH=N—, —N=C(CH$_3$)—, —C(CH$_3$)=N—, —N=N—, —C≡C— or —CH=N—N=CH—. When $Z^1$ is independently a single bond, —OCH$_2$—, —CH$_2$O—, —COO—, —OCO—, —CH$_2$CH$_2$—, —CH=CHCOO—, —OCOCH=CH—, —CH$_2$CH$_2$COO— or —OCOCH$_2$CH$_2$—, the solubility in the organic solvent is high, and the temperature range of the liquid crystal phase is easily widened, and therefore such a case is further preferred.

Then, m and n are independently an integer from 0 to 5, in which an expression: 1≤m+n≤8 holds. When m and n are independently 1, 2 or 3, the solubility in the organic solvent is high, and the temperature range of the liquid crystal phase is easily widened, and therefore such a case is further preferred.

$X^1$ is alkylene having 1 to 5 carbons or a derivative of alkylene. A crosslinking structure having a carbonyl group in α-position is formed in 2-position to 3-position of a 1,4-phenylene group in the polymerizable liquid crystal compound by $X^1$. The liquid-crystal-phase's lifetime is extended, and the temperature range in which the liquid crystal phase is formed in the range of 60° C. in 120° C. is wide, and therefore the crosslinking structure having the carbonyl group in α-position is preferred in 2-position to 3-positions of the 1,4-phenylene group.

In the alkylene derivative, for example, in alkylene having 1 to 5 carbons, at least one piece of —CH$_2$— can be replaced by —CO—, —S—, —O— or —NH—, and in the alkylene, at least one piece of —CH$_2$—CH$_2$— can be replaced by —CH=CH—, and at least one hydrogen in —CH$_2$—, —NH— and —CH= described above may be replaced by fluorine, chlorine, trifluoromethyl, alkyl having 1 to 10 carbons or alkanoyl having 1 to 10 carbons.

From a viewpoint of ease of preparation, $X^1$ is alkylene having 2 to 4 carbons, and in the alkylene, —CH$_2$— is replaced by —CO—, —S—, —O— or —NH—, and at least one hydrogen in —CH$_2$—, —NH— and —CH= described above is preferably alkylene that is replaced by fluorine, chlorine, trifluoromethyl, alkyl having 1 to 5 carbons or alkanoyl having 1 to 5 carbons.

One of $R^1$ is a polymerizable functional group, and the other of $R^1$ is a polymerizable functional group, hydrogen, fluorine, chlorine, trifluoromethyl, trifluoromethoxy, cyano, alkyl having 1 to 12 carbons, alkoxy having 1 to 12 carbons, alkenyl having 2 to 12 carbons, alkylester having 1 to 12 carbons or alkoxycarbonyl having 1 to 12 carbons.

Polymerization by light or heat is easy, and therefore the polymerizable functional group of $R^1$ is preferably replaced by a group represented by formula (2).

$$\xi\!-\!Y^1\!-\!Q^1\!-\!PG \qquad (2)$$

wherein, $Y^1$ is a single bond, —O—, —COO—, —OCO— or —OCOO—, and $Q^1$ is a single bond or alkylene having 1 to 20 carbons, and in the alkylene, at least one piece of —CH$_2$— may be replaced by —O—, —COO— or —OCO—, and PG is a functional group represented by any one of formula (PG-1) to formula (PG-9).

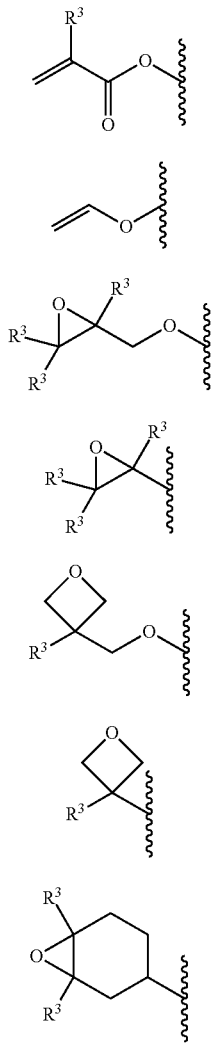

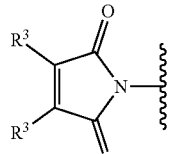

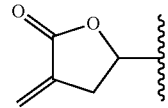

wherein, in formula (PG-1) to formula (PG-9), $R^3$ is independently hydrogen, halogen, methyl, ethyl or trifluoromethyl.

In the liquid crystal polymerized film obtained from the polymerizable liquid crystal composition, mechanical strength is excellent, and optical characteristics cause no change for a long period of time, and therefore both of $R^1$ in formula (1) are preferably a group represented by formula (2).

In formula (2), when $Q^1$ is alkylene having 1 to 20 carbons, the liquid crystal phase of the polymerizable liquid crystal composition is easily induced, and phase separation from any other liquid crystal compound and the organic solvent is hard to be caused.

PG is independently a functional group represented by any one of formula (PG-1) to formula (PG-9).

The functional group represented by formula (PG-1), formula (PG-8) and formula (PG-9) has a structure of α,β-unsaturated ketone, and therefore is a polymerizable functional group that is polymerized by various means to change the compound into a polymer having larger molecular weight.

The functional group represented by formula (PG-2) has a vinyl group adjacent to an electron donating group, and therefore is the polymerizable functional group that is polymerized by various means to change the compound into the polymer having larger molecular weight.

The functional group represented by formula (PG-3) to formula (PG-7) has cyclic ether having strain, and therefore is the polymerizable functional group that is polymerized by various means to change the compound into the polymer having larger molecular weight.

As the functional group represented by formula (PG-1) to formula (PG-9), a suitable functional group can be selected according to film production conditions. For example, when the film is prepared by ordinarily used photo-curing, an acrylic group or a methacrylic group represented by formula (PG-1) is preferred in view of high curability, solubility in the solvent, ease of handling or the like.

Specific examples of a polymerizable liquid crystal compound represented by formula (1) are shown in formula (1-1-1) to formula (1-1-14).

Compound (1) can be synthesized by combining publicly-known techniques in synthetic organic chemistry.

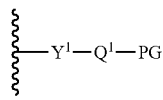

-continued
(1-1-2)
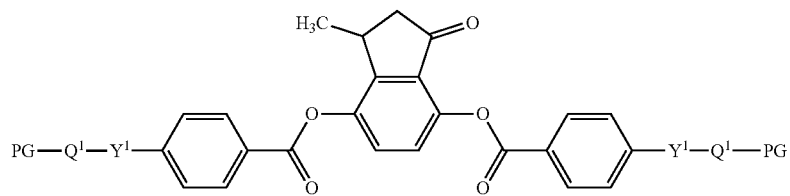
(1-1-3)
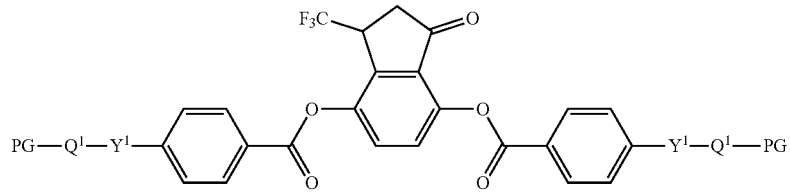
(1-1-4)
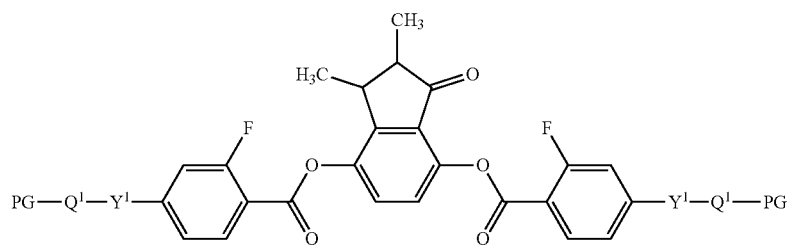
(1-1-5)
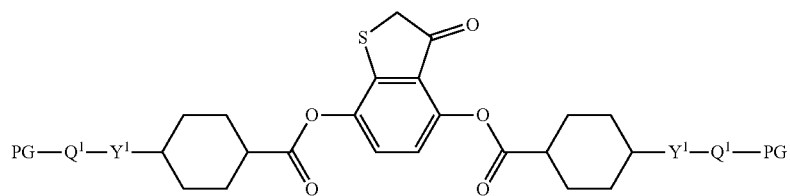
(1-1-6)
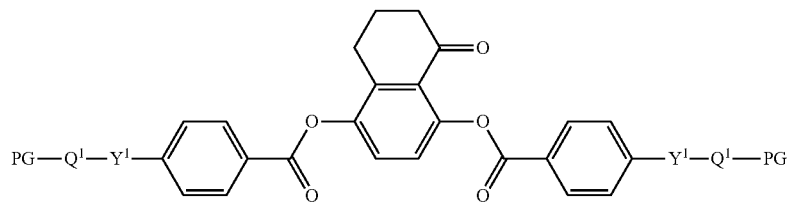
(1-1-7)
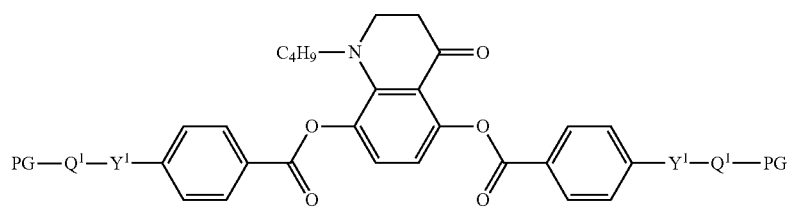
(1-1-8)
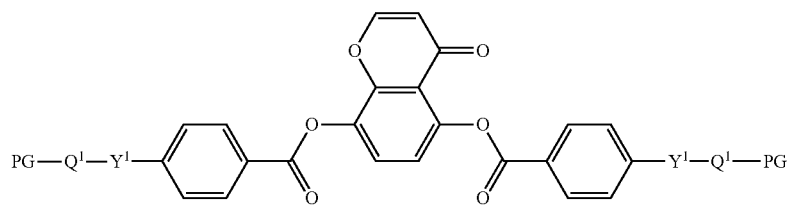

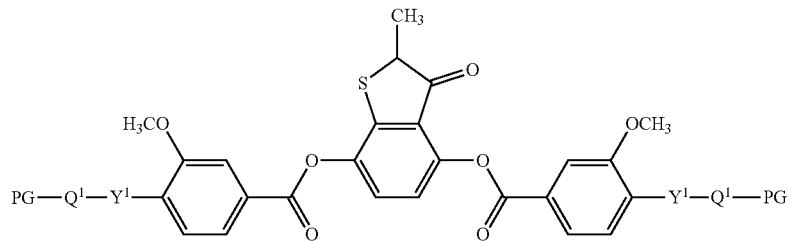
(1-1-9)
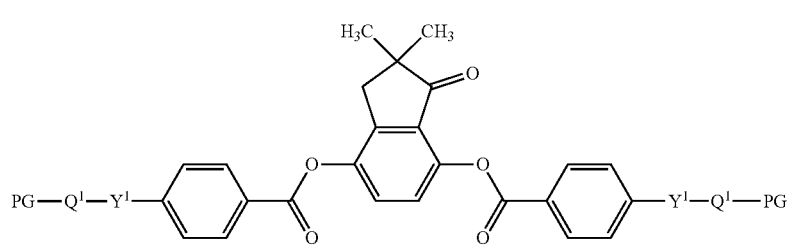
(1-1-10)
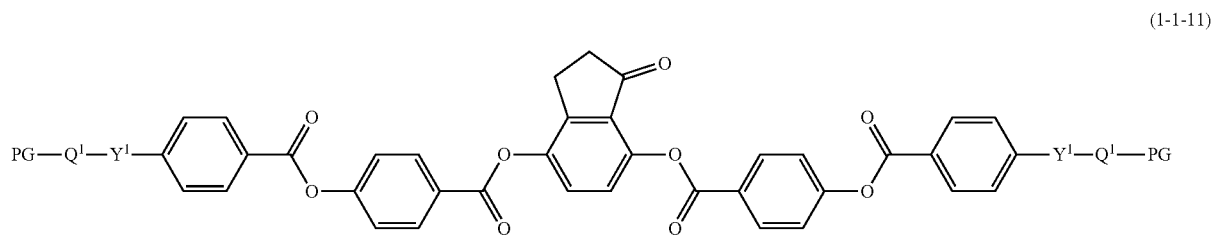
(1-1-11)
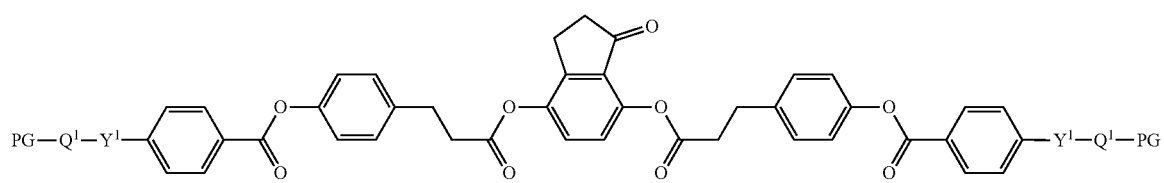
(1-1-12)
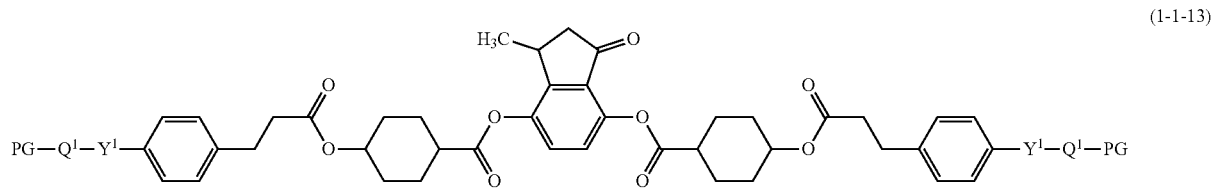
(1-1-13)
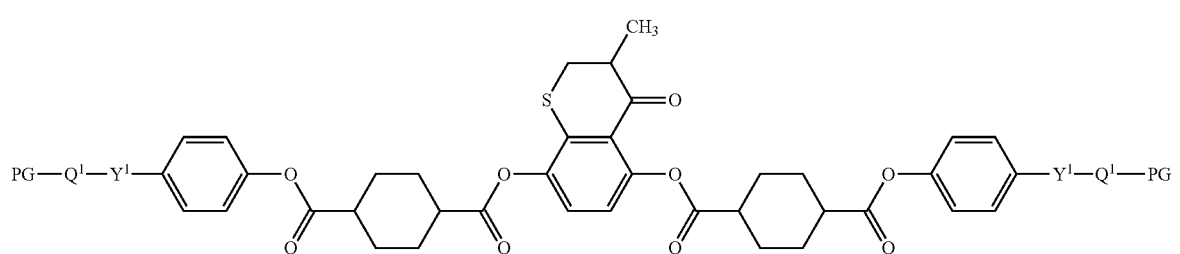
(1-1-14)

In formula (1-1-1) to formula (1-1-14), $Y^1$ is independently a single bond, —O—, —COO—, —OCO— or —OCOO—, and $Q^1$ is independently a single bond or alkylene having 1 to 20 carbons, and in the alkylene, at least one piece of —CH$_2$— may be replaced by —O—, —COO— or —OCO—, and PG is independently any one of functional groups represented by formula (PG-1) to formula (PG-9) described above.

2. Polymerizable Liquid Crystal Composition

A polymerizable liquid crystal composition of the invention contains at least one compound (1).

The polymerizable liquid crystal composition containing at least one compound (1) of the invention has a wide liquid crystal phase in the temperature range of 60° C. to 120° C., and liquid-crystal-phase's lifetime is long. In the polymerizable liquid crystal composition having the wide liquid crystal phase in the temperature range of 60° C. to 120° C. and the long liquid-crystal-phase's lifetime, a state in which the polymerizable liquid crystal composition on the substrate is aligned continues for a long time in preparation of the substrate-embedded liquid crystal polymer, and therefore the liquid crystal polymerized film is easily produced.

Therefore, the liquid crystal polymerized film is easily prepared by applying the polymerizable liquid crystal composition of the invention containing at least one compound (1) as the raw material.

The polymerizable liquid crystal composition of the invention has a wide liquid crystal phase in the temperature range of 60° C. to 120° C. and the liquid-crystal-phase's lifetime becomes longer, and therefore the polymerizable liquid crystal composition of the invention preferably contains 10 to 100% by weight of compound (1), and further preferably contains 30 to 70% by weight of compound (1), based on the total amount of the polymerizable liquid crystal compound.

Moreover, the polymerizable liquid crystal composition of the invention preferably contains 7 to 99% by weight of compound (1), and further preferably contains 21 to 69% by weight of compound (1), based on the total amount of the polymerizable liquid crystal composition.

The polymerizable liquid crystal composition of the invention may contain a polymerizable liquid crystal compound other than the polymerizable liquid crystal compound represented by compound (1). From viewpoints of development of the liquid crystal phase of the polymerizable liquid crystal composition and compatibility between compound (1) and the organic solvent, a compound represented by formula (M1), (M2) or (M3) described below is preferred as the polymerizable liquid crystal compound.

In formulas (M1), (M2) and (M3), $A^M$ is each independently any divalent group selected from 1,4-phenylene, 1,4-cyclohexylene, 1,4-cyclohexenylene, pyridine-2,5-diyl, 1,3-dioxane-2,5-diyl, naphthalene-2,6-diyl or fluorene-2,7-diyl, and in the divalent group, at least one hydrogen may be replaced by fluorine, chlorine, cyano, hydroxy, formyl, trifluoroacetyl, difluoromethyl, trifluoromethyl, alkyl having 1 to 5 carbons, alkoxy having 1 to 5 carbons, alkoxycarbonyl having 1 to 5 carbons or alkanoyl having 1 to 5 carbons, $Z^M$ is each independently a single bond, —OCH$_2$—, —CH$_2$O—, —COO—, —OCO—, —COS—, —SCO—, —OCOO—, —CONH—, —NHCO—, —CF$_2$O—, —OCF$_2$—, —CH$_2$CH$_2$—, —CF$_2$CF$_2$—, —CH=CHCOO—, —OCOCH=CH—, —CH$_2$CH$_2$COO—, —OCOCH$_2$CH$_2$—, —COOCH$_2$CH$_2$—, —CH$_2$CH$_2$OCO—, —CH=CH—, —N=CH—, —CH=N—, —N=C(CH$_3$)—, —C(CH$_3$)=N—, —N=N—, —C≡C—, —CH=N—N=CH— or —C(CH$_3$)=N—N=C(CH$_3$)—, $X^M$ is hydrogen, fluorine, chlorine, trifluoromethyl, trifluoromethoxy, cyano, alkyl having 1 to 20 carbons, alkenyl having 1 to 20 carbons, alkoxy having 1 to 20 carbons or alkoxycarbonyl having 1 to 20 carbons, $Y^M$ is independently a single bond, —O—, —COO—, —OCO— or —OCOO—, $Q^M$ is a single bond, —O—, —COO— or —OCO—, q is an integer from 1 to 6, c and d are each an integer from 0 to 3, in which an expression: 1≤c+d≤6 holds, a is an integer from 0 to 20, and $R^M$ is hydrogen or methyl.

If increase in front contrast of the liquid crystal polymerized film, and induction to the liquid crystal phase of the polymerizable liquid crystal composition serving as a raw material of the liquid crystal polymerized film, and prevention of phase separation from any other liquid crystal compound and the organic solvent in the composition are taken into consideration, a total of compounds represented by formula (M1) in the polymerizable liquid crystal composition is preferably 10 to 90% by weight, and further preferably 10 to 70% by weight, based on the total weight of compounds represented by formula (1) and formula (M1). Here, "front contrast" means a value obtained from the formula: (luminance in a crossed Nicol state)/(luminance in a parallel Nicol state) upon arranging the substrate-embedded liquid crystal polymerized film between two polarizing plates.

Specific examples of compound (M1) include compounds (M1-1) to (M1-10).

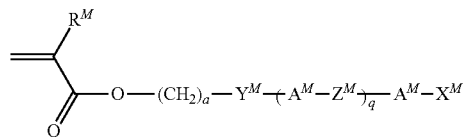

(M1)

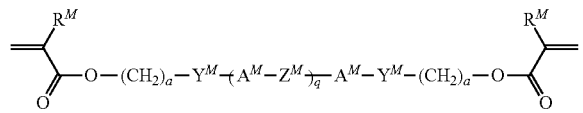

(M2)

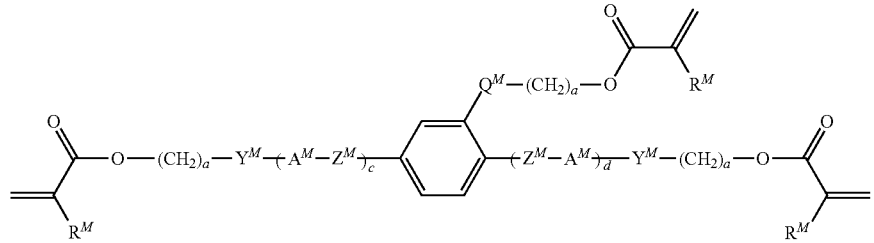

(M3)

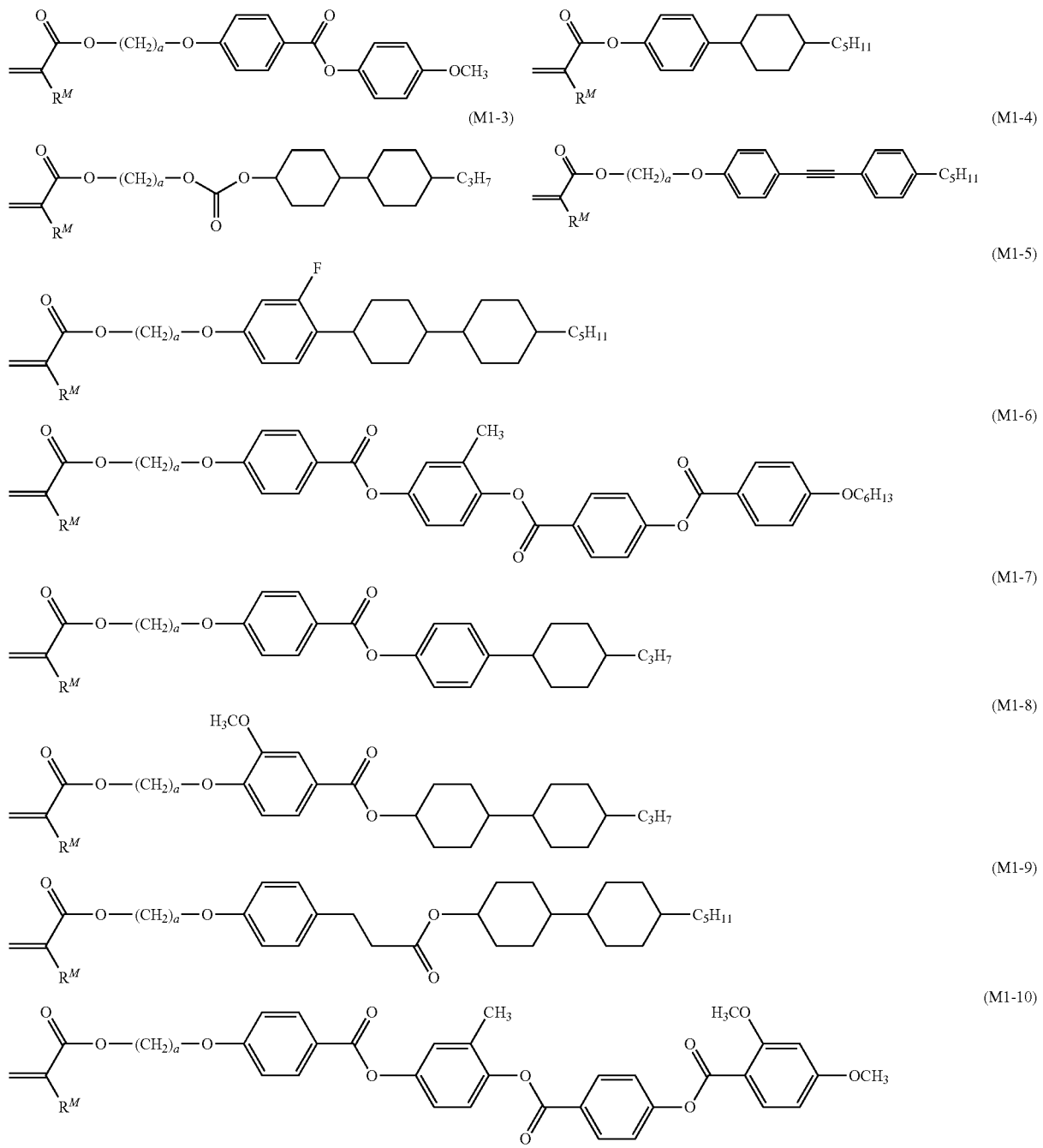
In formula (M1-1) to formula (M1-10), a is an integer from 1 to 12, and $R^M$ is hydrogen or methyl.
Specific examples of compound (M2) include compounds (M2-1) to (M2-10).
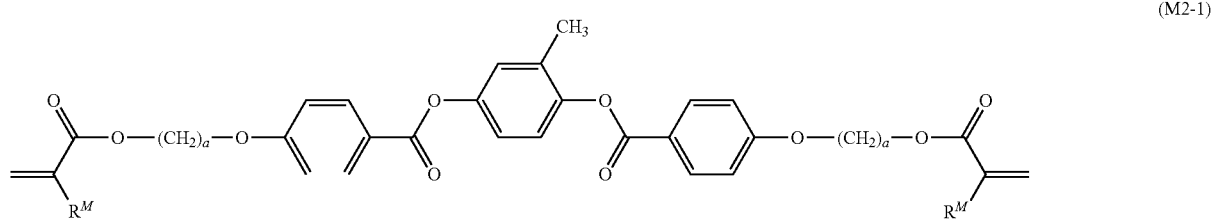

-continued
(M2-2)
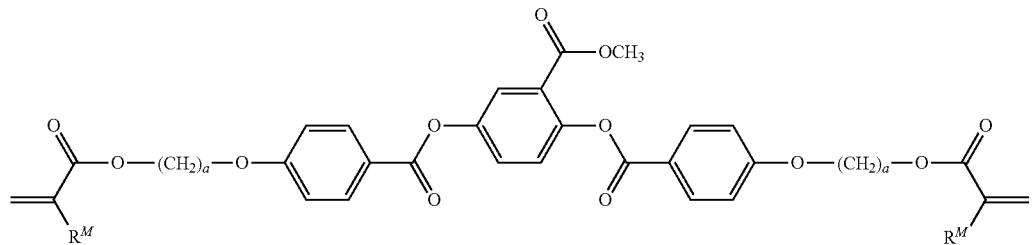
(M2-3)
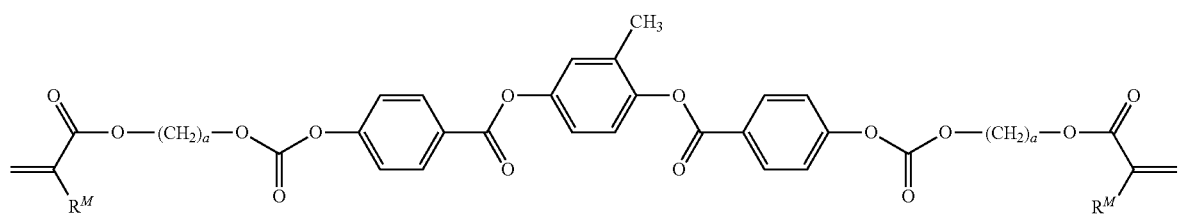
(M2-4)
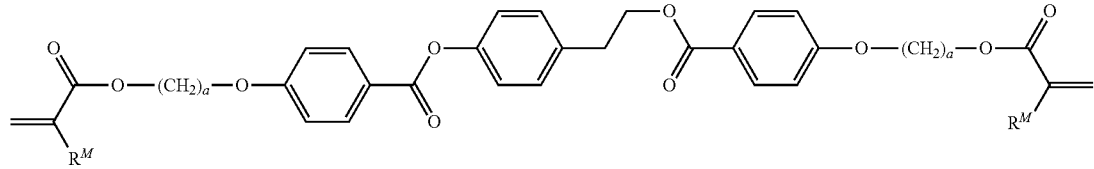
(M2-5)
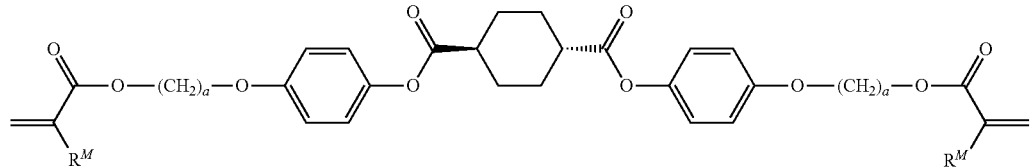
(M2-6)
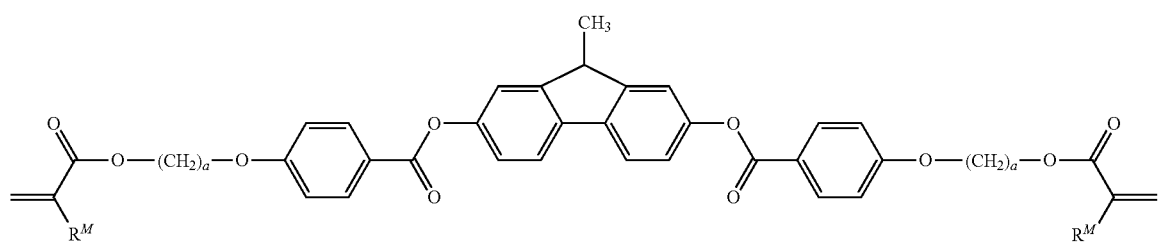
(M2-7)
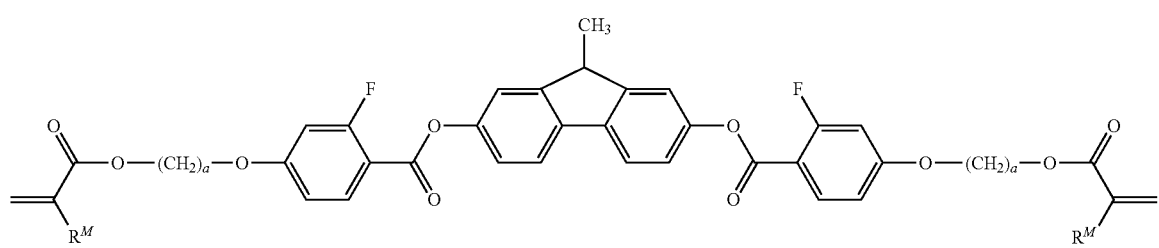
(M2-8)
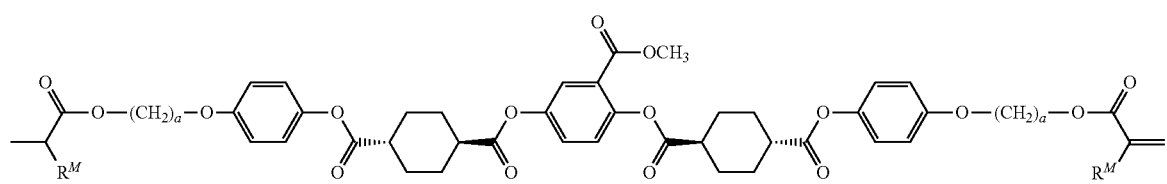

(M2-9)
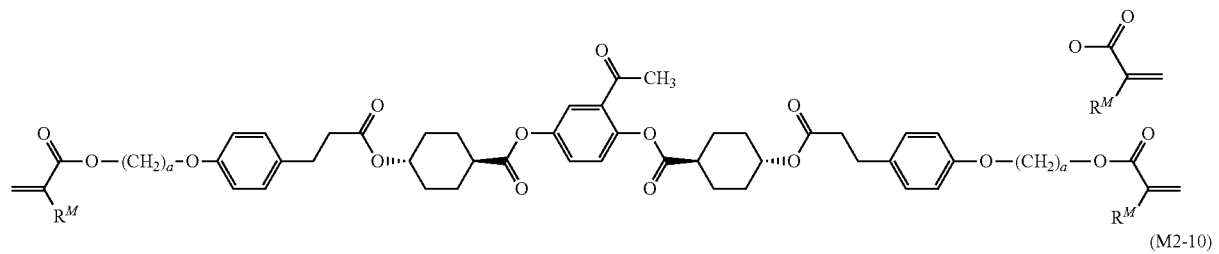
(M2-10)
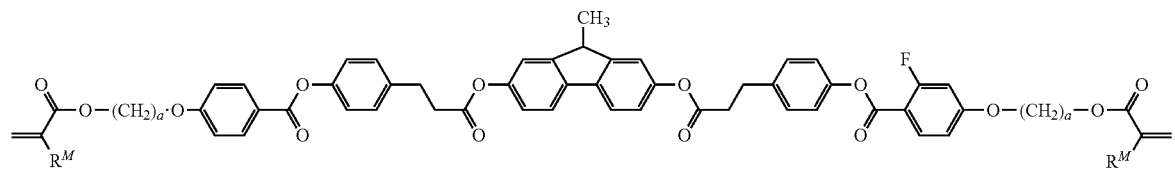
In formulas (M2-1) to (M2-10), a is an integer from 1 to 12, and $R^M$ is hydrogen or methyl.
Specific examples of compound (M3) include compounds (M3-1) to (M3-4).
(M3-1)
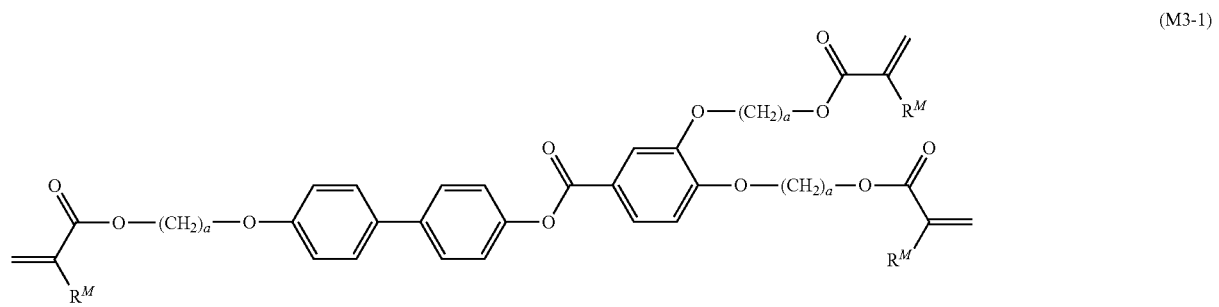
(M3-2)
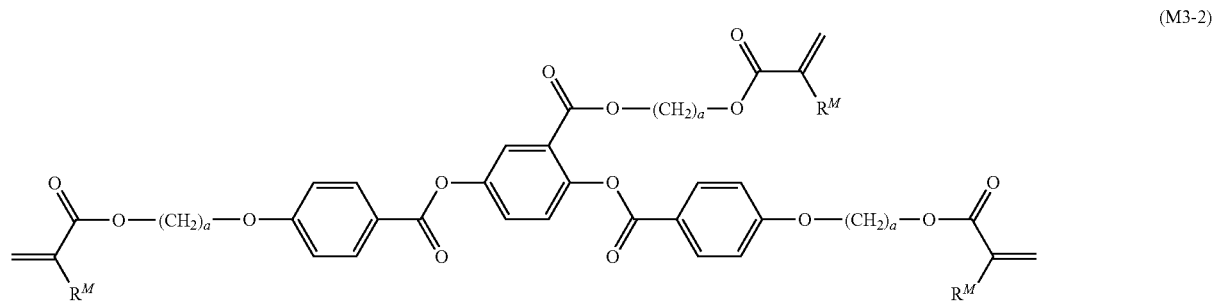
(M3-3)
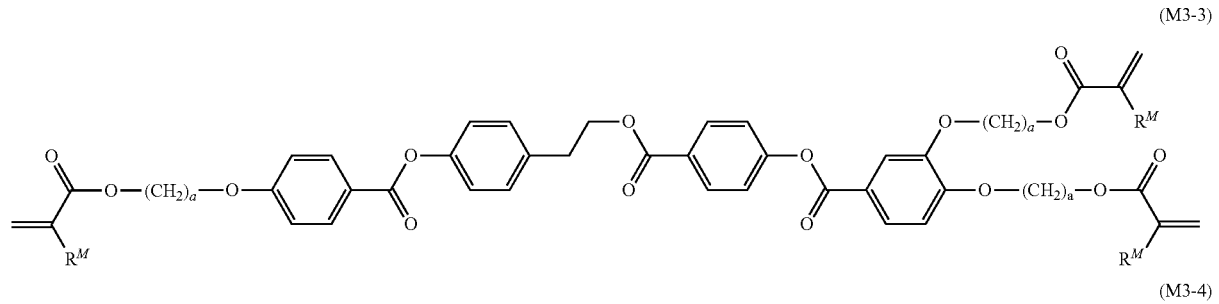
(M3-4)
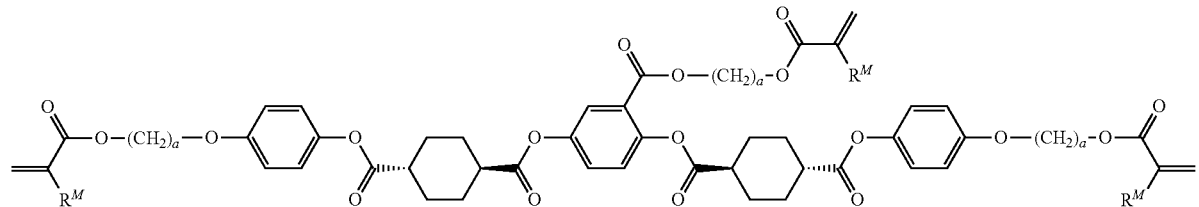

In formulas (M3-1) to (M3-4), a is an integer from 1 to 12, and $R^M$ is hydrogen or methyl.

Additive to Polymerizable Liquid Crystal Composition

The polymerizable liquid crystal composition of the invention may contain additive other than the polymerizable liquid crystal compound, unless the liquid crystal phase is lost.

Addition of a surfactant to the polymerizable liquid crystal composition causes improvement of smoothness of the liquid crystal polymerized film. Addition of a nonionic surfactant to the polymerizable liquid crystal composition causes further improvement of smoothness of the liquid crystal polymerized film. The surfactant is classified into an ionic surfactant and a nonionic surfactant.

The nonionic surfactant is effective in suppressing the tilt alignment of the liquid crystal polymerized film on a side of an air interface, and therefore preferred. Examples of the nonionic surfactant include a silicone-based nonionic surfactant, a fluorine-based nonionic surfactant, a vinyl-based nonionic surfactant and a hydrocarbon-based nonionic surfactant.

In order to improve the mechanical strength and chemical resistance of a surface of the liquid crystal polymerized film, the surfactant being the polymerizable compound may be added to the polymerizable liquid crystal composition. As the surfactant being the polymerizable compound, a surfactant in which a polymerization reaction is started with ultraviolet light is preferred.

Uniform alignment is easily formed in the liquid crystal polymerized film, and applicability of the polymerizable liquid crystal composition is improved, and therefore the surfactant in the polymerizable liquid crystal composition is preferably 0.01 to 5% by weight, and further preferably 0.05 to 1% by weight, based on the total amount of the polymerizable liquid crystal composition.

Examples of the silicone-based nonionic surfactant include a straight-chain polymer formed of siloxane bond, and a compound in which an organic group such as polyether and long-chain alkyl is introduced into a side chain and/or a terminal.

Examples of the fluorine-based nonionic surfactant include a compound having a perfluoroalkyl group or a perfluoroalkenyl group each having 2 to 7 carbons.

Examples of the vinyl-based nonionic surfactant include a (meth) acrylic polymer having a weight average molecular weight of 1,000 to 1,000,000.

The polymerizable liquid crystal composition of the invention may contain the non-liquid crystal polymerizable compound. In order to maintain the liquid crystal phase, the total weight of the non-liquid crystal polymerizable compound in the polymerizable liquid crystal composition is preferably 30% by weight or less based on the total amount of the polymerizable liquid crystal composition.

Reinforcement of the mechanical strength of the liquid crystal polymerized film, improvement of the chemical resistance or both thereof can be expected by addition of a polyfunctional non-liquid crystal polymerizable compound to the polymerizable liquid crystal composition.

As the non-liquid crystal polymerizable compound, a compound having one or two or more vinyl-based polymerizable functional groups is typical.

Improvement of adhesion between the liquid crystal polymer and the substrate can be expected by addition of the non-liquid crystal polymerizable compound having a polar group in a side chain and/or at a terminal to the polymerizable liquid crystal composition.

Examples of the non-liquid crystal polymerizable compound being the monofunctional compound include styrene, nucleus-substituted styrene, acrylonitrile, vinyl chloride, vinylidene chloride, vinylpyridine, N-vinyl pyrrolidone, vinylsulfonic acid, fatty acid vinyl, α,β-ethylenic unsaturated carboxylic acid, alkyl ester of (meth)acrylic acid in which the number of carbon atoms of alkyl is 1 to 18, hydroxy alkyl ester of (meth)acrylic acid in which the number of carbon atoms of hydroxyalkyl is 1 to 18, amino alkyl ester of (meth)acrylic acid in which the number of carbon atoms of amino alkyl is 1 to 18, ether oxygen-containing alkyl ester of (meth)acrylic acid in which the number of carbon atoms of ether oxygen-containing alkyl is 3 to 18, N-vinylacetamide, vinyl p-t-butyl benzoate, vinyl N,N-dimethylaminobenzoate, vinyl benzoate, vinyl pivalate, vinyl 2,2-dimethylbutanoate, vinyl 2,2-dimethylpentanoate, vinyl 2-methyl-2-butanoate, vinyl propionate, vinyl stearate, vinyl 2-ethyl-2-methylbutanoate, dicyclopentanyloxylethyl (meth)acrylate, isobornyloxylethyl (meth)acrylate, isobornyl (meth)acrylate, adamantyl (meth)acrylate, dimethyladamantyl (meth)acrylate, dicyclopentanyl (meth)acrylate, dicyclopentenyl (meth)acrylate, 2-acryloyloxy ethyl succinate, 2-acryloyloxyethyl hexahydrophthalic acid, 2-acryloyloxyethyl phthalic acid, 2-acryloyloxyethyl-2-hydroxyethyl phthalic acid, 2-acryloyloxyethyl acid phosphate, 2-methacryloyloxyethyl acid phosphate, polyethylene glycol having a polymerization degree of 2 to 100, polypropylene glycol, mono(meth)acrylate or di(meth)acrylate of polyalkylene glycol such as a copolymer between ethylene oxide and propylene oxide, or polyethylene glycol having a polymerization degree of 2 to 100 and capped with alkyl having 1 to 6 carbons at a terminal and mono(meth)acrylate of polyalkylene glycol being a copolymer among polypropylene glycol, ethylene oxide and propylene oxide. Examples of "fatty acid vinyl ester" include vinyl acetate. Examples of "α,β-ethylenic unsaturated carboxylic acid" include acrylic acid, methacrylic acid, maleic acid, fumaric acid and itaconic acid. Examples of "ether oxygen-containing alkyl ester of (meth)acrylic acid in which the number of carbon atoms of ether oxygen-containing alkyl is 3 to 18" include methoxyethyl ester, ethoxyethyl ester, methoxypropyl ester, methylcarbyl ester, ethylcarbyl ester and butylcarbyl ester.

Examples of a bifunctional non-liquid crystal polymerizable compound include 1,4-butanediol diacrylate, 1,6-hexanediol diacrylate, 1,9-nonanediol diacrylate, neopentyl glycol diacrylate, dimethylol tricyclodecane diacrylate, triethylene glycol diacrylate, dipropylene glycol diacrylate, tripropylene glycol diacrylate, tetraethylene glycol diacrylate, bisphenol A EO-added diacrylate, bisphenol A glycidyl diacrylate, polyethylene glycol diacrylate and a methacrylate compound thereof.

Examples of a trifunctional or higher functional polyfunctional non-liquid crystal polymerizable compound include pentaerythritol triacrylate, trimethylolpropane triacrylate, trimethylol EO-added triacrylate, trisacryloyloxyethyl phosphate, tris(acryloyloxyethyl) isocyanurate, alkyl-modified dipentaerythritol triacrylate, EO-modified trimethylolpropane tricrylate, PO-modified trimethylolpropane triacrylate, pentaerythritol tetraacrylate, alkyl-modified dipentaerythritol tetraacrylate, ditrimethylolpropane tetraacrylate, dipentaerythritol hexaacrylate, dipentaerythritolmonohydroxy pentaacrylate, alkyl-modified dipentaerythritol pentaacrylate, pentaerythritol trimetaacrylate, trimethylolpropane trimetacrylate, trimethylol EO-added trimetaacrylate, trismethacryloyloxy ethyl phosphate, trismethacryloyloxy ethyl isocyanurate, alkyl-modified dipentaerythritol trimetaacrylate, EO-modified trimethylolpropane trimethacrylate, PO-modified trimethylolpropane trimethacrylate, pentaerythritol tetramethacrylate, alkyl-modified dipentaerythritol tetramethacrylate, ditrimethylolpropane tetramethacrylate, dipentaerythritol hexamethacrylate, dipentaerythritolmonohydroxy pentamethacrylate and alkyl-modified dipentaerythritol pentamethacrylate.

Addition of a polymerizable compound having a bisphenol structure or cardo structure to the polymerizable liquid crystal composition causes improvement of degree of cure of the polymer and induction of homeotropic alignment of the liquid crystal polymerized film.

Examples of a polymerizable fluorene derivative having the cardo structure include a compound represented by formula (α-1) to formula (α-3).

Addition of a polymerization initiator causes optimization of a polymerization velocity of the polymerizable liquid crystal composition. From ease of a curing process, the polymerization initiator is preferably a photopolymerization initiator. The photopolymerization initiator is classified into a photoradical polymerization initiator, a photocationic polymerization initiator and a photoanionic polymerization initiator.

As a polymerizable liquid crystal compound having an acrylic group or a methacrylic group, the photoradical polymerization initiator is preferably used. As a polymerizable liquid crystal compound having an epoxy group or an oxetanyl group, the photocationic polymerization initiator or the photoanionic polymerization initiator is preferably used.

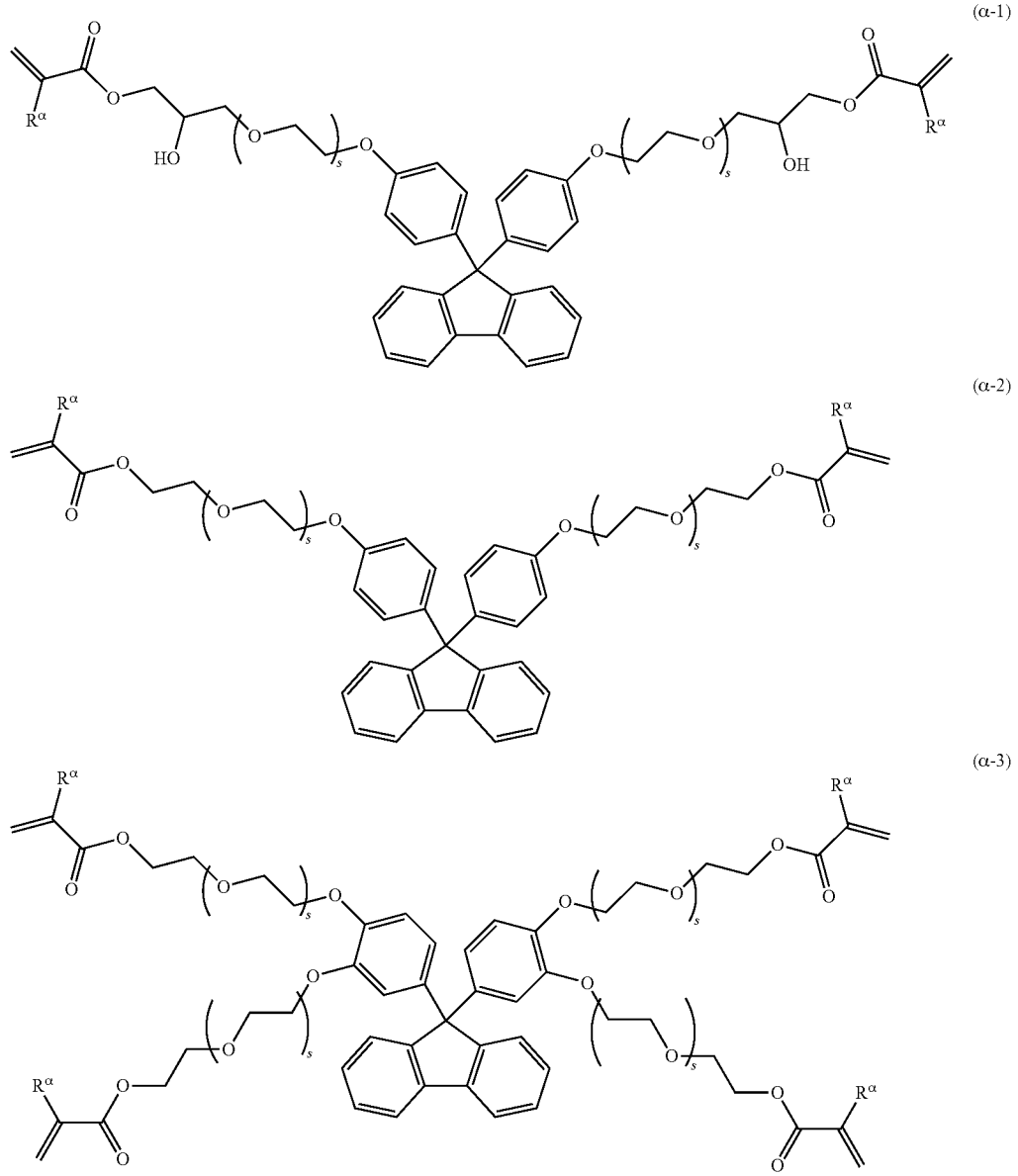

In formula (α-1) to formula (α-3), $R^\alpha$ is independently hydrogen or methyl, and s is independently an integer from 0 to 4.

Examples of the photoradical polymerization initiator include a benzoin ether-based photopolymerization initiator, a benzyl ketal-based photopolymerization initiator, an acetophenone-based photopolymerization initiator, an acylphosphine oxide-based photopolymerization initiator, an oxime ester-based photopolymerization initiator and a hydrogen abstraction type polymerization initiator.

Examples of the acetophenone-based photopolymerization initiator include isobutyl benzoin ether, isopropyl benzoin ether, 2,2-dimethoxy-1,2-diphenylethane-1-one, 2-hydroxy-2-methyl-1-phenylpropane-1-one, 1-hydroxycyclohexylphenyl ketone, 1-[4-(2-hydroxyethoxy)phenyl]-2-hydroxy-2-methyl-1-propane-1-one, 2-hydroxy-1-[4-[4-(2-hydroxy-2-methylpropionyl)benzyl]phenyl]-2-methylpropane-1-one, 2-hydroxy-2-methyl-1-(4-isopropylphenyl)-propane-1-one, 2-methyl-1-[4-(methylthio)phenyl]-2-morpholinopropane-1-one, 2-benzyl-2-dimethylamino-1-(4-morpholinophenyl)-butane-1-one and 2-dimethylamino-2-(4-methyl-benzyl)-1-(4-morpholinophenyl)-butane-1-one.

Examples of the acylphosphine oxide-based photopolymerization initiator include bis(2,4,6-trimethylbenzoyl)-phenylphosphine oxide, bis(2,6-dimethoxybenzoyl)-2,4,4-trimethyl-pentylphosphine oxide and 2,4,6-trimethylbenzoyl-diphenylphosphine oxide.

Examples of the oxime ester-based photopolymerization initiator include 2-(benzoyloxyimino)-1-[4-(phenylthio)phenyl]-1-octanone, and 1,2-Propanedione,1-(4-{[4-(2-hydroxyethoxy)phenyl]thio}phenyl)-,2-(O-acetyloxime).

Examples of the hydrogen abstraction type polymerization initiator include benzophenone, oxyphenylacetic acid, 2-[2-oxo-2-phenylacetoxyethoxy]ethyl ester, oxyphenylacetic acid, 2-(2-hydroxyethoxy)ethyl ester and 2-oxo-2-phenylacetic acid methyl ester.

Examples of the photocationic polymerization initiator include a sulfonium salt-based photopolymerization initiator, an iodonium salt photopolymerization initiator and a triazine-based photopolymerization initiator.

Examples of the sulfonium salt-based photopolymerization initiator include tri(4-methylphenyl)sulfonium trifluoromethanesulfonate, tri(4-methylphenyl)sulfonium hexafluorophosphate and (biphenyl) [4-(phenylthio)phenyl] sulfonium hexafluorophosphate.

Examples of the iodonium salt photopolymerization initiator include (4-methylphenyl) [4-(2-methylpropyl)phenyl] iodonium hexafluorophosphate and bis(4-t-butylphenyl)iodonium hexafluorophosphate.

Examples of the triazine-based photopolymerization initiator include
2-(4-methoxyphenyl)-4,6-bis(trichloromethyl)-1,3,5-triazine,
4-(3,4-dimethoxyphenyl)-2,6-bis(trichloromethyl)-1,3,5-triazine and
2,4-bis(trichloromethyl)-6-(2,4-dimethoxy)styryl-1,3,5-triazine.

Examples of the photoanionic polymerization initiator include an ionic photopolymerization initiator and a nonionic polymerization initiator.

Examples of the ionic photopolymerization initiator include 1,2-diisopropyl-3-[bis(dimethylamino)methylene]guanidium 2-(3-benzoylphenyl)propionate and 1,5,7-triazabicyclo[4.4.0]deca-5-ene 2-(9-oxoxanthene-2-yl)propionate.

Examples of the nonionic polymerization initiator include 2-nitrophenylmethyl 4-methacryloyloxy piperidine-1-carboxylate, 9-anthrylmethyl N,N-diethyl carbamate, acetophenone-ortho-benzoyloxime, cyclohexylcarbamic acid 2-nitrobenzyl, cyclohexylcarbamic acid 1,2-bis(4-methoxyphenyl)-2-oxoethyl, 1-(anthraquinone-2-yl) ethylimidazole carboxylate and 1-piperidine-3-(2-hydroxyphenyl)-2-propane-1-one.

From viewpoints of contrast, stickiness prevention and prevention of change over time of retardation of the liquid crystal polymerized film, the total weight of the photopolymerization initiator contained in the polymerizable liquid crystal composition is preferably 1 to 30% by weight, further preferably 1 to 15% by weight, and still further preferably 3 to 10% by weight, based on the total amount of the polymerizable liquid crystal composition.

A sensitizer may be added to the polymerizable liquid crystal composition together with the photopolymerization initiator. Examples of the sensitizer include isopropylthioxanthone, diethylthioxanthone, ethyl-4 dimethylaminobenzoate and 2-ethylhexyl-4-dimethylaminobenzoate.

A reaction rate of the polymerizable liquid crystal compound and a length of a chain of the polymer in the liquid crystal polymerized film can be adjusted by addition of a chain transfer agent to the polymerizable liquid crystal composition.

The reaction rate of the polymerizable liquid crystal compound is reduced by increase of an amount of the chain transfer agent. The length of the chain of the polymer is decreased by increase of the amount of the chain transfer agent.

Examples of the chain transfer agent include a thiol derivative and a styrene dimer derivative.

Examples of a monofunctional thiol derivative include dodecanethiol and 2-ethylhexyl-(3-mercapto)propionate.

Examples of a polyfunctional thiol derivative include trimethylolpropanetris(3-mercaptopropionate), pentaerythritol tetrakis(3-mercaptopropionate), 1,4-bis(3-mercaptobutyryloxy)butane, pentaerythritol tetrakis(3-mercaptobutyrate) and 1,3,5-tris(3-mercaptobutyloxyethyl)-1,3,5-triazine-2,4,6(1H,3H,5H)-trione.

Examples of a styrene dimer-based chain transfer agent include 2,4-diphenyl-4-methyl-1-pentene and 2,4-diphenyl-1-butene.

Addition of a polymerization inhibitor to the polymerizable liquid crystal composition causes prevention of polymerization start during storage of the polymerizable liquid crystal composition. Examples of the polymerization inhibitor include a phenol derivative, a phenothiazine derivative, a compound having a nitroso group and a benzothiazine derivative.

Examples of the polymerization inhibitor being the phenol derivative include 2,5-di(t-butyl)hydroxytoluene, hydroquinone, o-hydroxybenzophenone, methylene blue and diphenyl picryl hydrazide.

Examples of the polymerization inhibitor being the phenothiazine derivative include phenothiazine and methylene blue.

Examples of the polymerization inhibitor being the compound having the typical nitroso group include N,N-dimethyl-4-nitrosoaniline.

Addition of a polymerization inhibitor to the polymerizable liquid crystal composition causes suppression of the polymerization reaction in the polymerizable liquid crystal composition by generation of radicals in the polymerizable liquid crystal composition. Addition of the polymerization inhibitor causes improvement of storage stability of the polymerizable liquid crystal composition.

The polymerization inhibitor is (a) a phenol-based antioxidant, (b) a sulfur-based antioxidant, (c) a phosphoric acid-based antioxidant and (d) a hindered amine-based antioxidant. From a viewpoint of compatibility with the polymerizable liquid crystal composition, or transparency of the liquid crystal polymerized film, the phenol-based antioxidant is preferred. From a viewpoint of compatibility, a phenol-based antioxidant having a t-butyl group in an ortho position of a hydroxy group is preferred.

Addition of an ultraviolet light absorber to the polymerizable liquid crystal composition causes improvement of weather resistance of liquid crystal polymerized films.

Addition of a light stabilizer to the polymerizable liquid crystal composition causes improvement of the weather resistance of the liquid crystal polymerized films.

Addition of an antioxidant to the polymerizable liquid crystal composition causes improvement of the weather resistance of the liquid crystal polymerized films.

Addition of a silane coupling agent to the polymerizable liquid crystal composition causes improvement of adhesion between the substrate and the liquid crystal polymerized film.

The polymerizable liquid crystal composition of the invention may contain a compound having optical activity. Addition of the compound having optical activity to the liquid crystal composition causes induction of the liquid crystal polymerized film into twist alignment. The liquid crystal polymerized film can be used in the form of a selective reflection film and a negative C-plate in a wavelength region of 300 to 2,000 nanometers.

Specific examples of the compound having optical activity include a compound having asymmetric carbon, an axially chiral compound having a structure such as a binaphtyl structure and a helicene structure, and a planar chiral compound having a structure such as a cyclophane structure. From a viewpoint of immobilizing a helical pitch of twist alignment, the compound having optical activity in the above case is preferably a polymerizable compound.

The liquid crystal polymerized film of the invention may contain a dichroic dye. The liquid crystal polymerized film combined with the dichroic dye can be used in the form of an absorptive polarizing plate.

The dichroic dye preferably has a maximum absorption wavelength in the range of 300 to 700 nanometers. An acridine dye, an oxazine dye, a cyanine dye, a naphthalene dye, an azo dye, an anthraquinone pigment or the like can be utilized. Examples of the dichroic dye include, as the azo dye, a monoazo dye, a bis-azo dye, a tris-azo dye, a tetrakis-azo dye and a stilbene-azo dye.

The liquid crystal polymerized film of the invention may contain a fluorescent dye. The liquid crystal polymerized film combined with the fluorescent dye can be used in the form of a polarized light-emitting film and a wavelength conversion film.

Polymerizable Liquid Crystal Composition Solution

In order to facilitate coating onto the substrate, a solvent is preferably added to the polymerizable liquid crystal composition.

From a viewpoint of compatibility between the polymerizable liquid crystal compound and the solvent, a content of the polymerizable liquid crystal composition in the polymerizable liquid crystal composition solution is preferably 5 to 50% by weight, and further preferably 15 to 40% by weight.

Such a solvent serves as the component of the solvent as an ester-based solvent, an amide-based solvent, an alcohol-based solvent, an ether-based solvent, a cyclic ether-based solvent, an aromatic hydrocarbon-based solvent, a halogenated aromatic hydrocarbon-based solvent, an aliphatic hydrocarbon-based solvent, a halogenated aliphatic hydrocarbon-based solvent, an alicyclic hydrocarbon-based solvent, a ketone-based solvent and an acetate-based solvent.

The ester-based solvent means a compound having an ester bond, and serving as a component of the solvent.

Examples of the ester-based solvent include alkyl acetate, ethyl trifluoroacetate, alkyl propionate, alkyl butyrate, dialkyl malonate, alkyl glycolate, alkyl lactate, monoacetin, γ-butyrolactone and γ-valerolactone.

Examples of alkyl acetate include methyl acetate, ethyl acetate, propyl acetate, isopropyl acetate, butyl acetate, 3-methoxybutyl acetate, isobutyl acetate, pentyl acetate and isopentyl acetate.

Examples of alkyl propionate include methyl propionate, methyl 3-methoxypropionate, ethyl propionate, propyl propionate and butyl propionate.

Examples of alkyl butyrate include methyl butyrate, ethyl butylate, butyl butyrate, isobutyl butyrate and propyl butyrate.

Examples of dialkyl malonate include diethyl malonate.

Examples of alkyl glycolate include methyl glycolate and ethyl glycolate.

Examples of alkyl lactate include methyl lactate, ethyl lactate, isopropyl lactate, n-propyl lactate, butyl lactate and ethylhexyl lactate.

The amide-based solvent means a compound having an amide bond, and serving as a component of the solvent.

Examples of the amide-based solvent include N-methyl-2-pyrrolidone, N,N-dimethylacetamide, N-methylpropionamide, N,N-dimethylformamide, N,N-diethylformamide, N,N-diethylacetamide, N,N-dimethylacetamide dimethyl acetal, N-methylcaprolactam and 1,3-dimethyl-2-imidazolidinone.

The alcohol-based solvent means a compound having a hydroxy group, and serving as a component of the solvent.

Examples of alcohol include methanol, ethanol, 1-propanol, 2-propanol, 1-methoxy-2-propanol, t-butyl alcohol, sec-butyl alcohol, butanol, 3-methoxybutanol, 2-ethylbutanol, n-hexanol, n-heptanol, n-octanol, 1-dodecanol, ethylhexanol, 3,5,5-trimethylhexanol, n-amyl alcohol, hexafluoro-2-propanol, glycerol, ethylene glycol, diethylene glycol, triethylene glycol, tetraethylene glycol, propylene glycol, dipropylene glycol, tripropylene glycol, hexylene glycol, 1,3-butanediol, 1,4-butanediol, 2,3-butanediol, 1,5-pentanediol, 2,4-pentanediol, 2,5-hexanediol, 3-methyl-3-methoxybutanol, cyclohexanol, methyl cyclohexanol, ethylene glycol monomethyl ether, ethylene glycol monoisopropyl ether, ethylene glycol monobutyl ether, ethylene glycol monoisobutyl ether, diethylene glycol monomethyl ether, diethylene glycol monoethyl ether, triethylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropyleneglycol monopropyl ether, dipropyleneglycol monobutyl ether, terpineol and dihydroterpineol.

The ether-based solvent means a compound having an ether bond, and serving as a component of the solvent.

Examples of the ether-based solvent include ethylene glycol dimethyl ether, ethylene glycol diethyl ether, diethylene glycol dimethyl ether, diethylene glycol diethyl ether, diethylene glycol dibutyl ether, triethylene glycol dimethyl ether, bis(2-propyl) ether, diethylene glycol methyl ethyl ether, dipropylene glycol dimethyl ether, anisole, cyclopentyl methyl ether and methyl t-butyl ether.

The cyclic ether-based solvent means a cyclic compound having an ether bond, and serving as a component of the solvent.

Examples of the cyclic ether-based solvent include 1,4-dioxane, 1,3-dioxolane and tetrahydrofuran.

The aromatic hydrocarbon-based solvent means a compound having aromatic hydrocarbon, and serving as a component of the solvent.

Examples of the aromatic hydrocarbon-based solvent include benzene, toluene, xylene, mesitylene, ethylbenzene, diethylbenzene, i-propylbenzene, n-propylbenzene, t-butylbenzene, s-butylbenzene, n-butylbenzene and tetralin.

The halogenated aromatic hydrocarbon-based solvent means chlorobenzene, 1,2-dichlorobenzene or the like.

The aliphatic hydrocarbon-based solvent means hexane, heptane, myrcene or the like.

The halogenated aliphatic hydrocarbon-based solvent means chloroform, dichloromethane, carbon tetrachloride, dichloroethane, trichloroethylene, tetrachloroethylene or the like.

The alicyclic hydrocarbon-based solvent means alicyclic hydrocarbon such as cyclohexane, cycloheptane, decalin, α-pinene, β-pinene and D-limonene.

The ketone-based solvent means a compound having a ketone structure, and serving as a component of the solvent.

Examples of the ketone-based solvent include acetone, methyl ethyl ketone, methyl isobutyl ketone, cyclohexanone, cyclopentanone and methyl propyl ketone.

The acetate-based solvent means a compound having an acetoxy group, and serving as a component of the solvent.

Examples of the acetate-based solvent include ethylene glycol monomethyl ether acetate, ethylene glycol monobutyl ether acetate, diethylene glycol monoethyl ether acetate, propylene glycol monomethyl ether acetate, propylene glycol monoethyl ether acetate, propylene glycol monobutyl ether acetate, methyl acetoacetate and 1-methoxy-2-propyl acetate.

Substrate

Examples of a material of the substrate include glass, plastics, and metal. Slit-form processing may be applied onto the glass or the metal. Stretching treatment and surface treatment such as hydrophilizing treatment and hydrophobicizing treatment may be applied onto the plastics.

When the liquid crystal polymerized film having homogeneous alignment and tilt alignment is formed on the substrate, surface treatment is applied to the substrate before the polymerizable liquid crystal composition is applied to the substrate to induce alignment in the liquid crystal polymerized film. Specific examples of the surface treatment include a method such as rubbing treatment and irradiation with linearly polarized ultraviolet light.

3. Liquid Crystal Polymerized Film

The liquid crystal polymerized film prepared by using the polymerizable liquid crystal composition as the raw material according to the invention has no alignment defects, and is easily prepared, and birefringence of the liquid crystal polymer in the liquid crystal polymerized film is high, and therefore the liquid crystal polymerized films according to the tenth to twelfth aspects each have no alignment defects and can be thinned while production cost is suppressed.

Various coating methods are used for coating the polymerizable liquid crystal composition solution thereon. From a viewpoint of uniformity of a film thickness of the polymerizable liquid crystal composition on the substrate, as a coating method, a spin coating method, a microgravure coating method, a gravure coating method, a wire-bar coating method, a dip coating method, a spray coating method, a meniscus coating method and a die coating method are preferred.

Heat treatment during drying upon forming the substrate-embedded liquid crystal polymer is preferably applied thereto for removing the solvent. The heat treatment can be applied thereto by using a hot plate or a drying oven, or blowing warm air or hot air, or the like.

A means such as an electron beam, ultraviolet light, visible light and infrared light can be utilized for obtaining the liquid crystal polymerized film of the invention. A wavelength range of irradiation light for obtaining the liquid crystal polymerized film is 150 to 500 nanometers. A preferred wavelength range of irradiation light is 250 to 450 nanometers, and a further preferred range is 300 to 400 nanometers.

As a light source of the light, a low-pressure mercury lamp, a high-pressure discharge lamp and a short arc discharge lamp can be utilized. Specific examples of the low-pressure mercury lamp include a bactericidal lamp, a fluorescent chemical lamp and a black light. Specific examples of the high-pressure discharge lamp include a high pressure mercury lamp and a metal halide lamp. Specific examples of the short arc discharge lamp include an ultra-high pressure mercury lamp, a Xenon lamp and a Mercury-Xenon lamp.

When an alignment film is formed on the substrate and the polymerizable liquid crystal compound contained in the polymerizable liquid crystal composition is aligned by the alignment film, and then the polymerizable liquid crystal compound is polymerized, surface treatment is applied to the alignment film. Specific examples of the surface treatment include a method such as rubbing and irradiation with polarized ultraviolet light.

The procedures described below are one example of formation of the alignment film on the substrate and the rubbing treatment.

(1) A solution of an aligning agent is applied to a substrate to form a coating film.

(2) Heat treatment is applied to the substrate having the coating film obtained.

(3) rubbing cloth formed of a raw material such as rayon, cotton and polyamide is wound around a metallic roll or the like;

(4) the roll is brought into contact with the substrate; and (5) the roll is moved in parallel to a surface of the substrate while the roll is rotated, or the substrate is moved with keeping immobilizing the roll.

As the aligning agent, the solution containing polyimide, polyamic acid, polyvinyl alcohol or the like is used.

The procedures described below are one example of formation of the alignment film on the substrate and irradiation with polarized ultraviolet light.

(1) A solution of an aligning agent is applied to a substrate to form a coating film.

(2) Heat treatment is applied to the substrate having the coating film obtained.

(3) On the substrate, the substrate is irradiated with linearly polarized light at a wavelength of 250 to 400 nanometers; and (4) when necessary, heat treatment is applied thereto.

As the aligning agent, the solution containing polyimide having a photosensitive group, polyamic acid, a cycloolefin polymer, polyacrylate or the like is used. Specific examples of the photosensitive group include chalcone, cinnamate, cinnamoyl, stilbene, cyclobutane or azobenzene.

In the liquid crystal polymerized film of the invention, the substrate-embedded liquid crystal polymer having no alignment defects is easily prepared.

In the liquid crystal polymerized film of the invention, birefringence of the liquid crystal polymer in the liquid crystal polymerized film is high, and therefore optical characteristics can be realized by using a thinner liquid crystal polymer. Therefore, a thinner liquid crystal polymerized film can be provided, and the production cost can be suppressed.

The liquid crystal polymerized film of the invention can be exclusively utilized as the phase difference film.

The phase difference film of the invention has no alignment defects.

In the phase difference film of the invention, operation in steps of preparation of the liquid crystal polymerized film is easy, and therefore the production cost can be suppressed.

In the phase difference film of the invention, birefringence of the liquid crystal polymer is high, and therefore the thickness can be further reduced.

A highly functional polarizing plate having a function of optical compensation or the like can be produced by applying the polarizing plate as the substrate and forming the liquid crystal polymerized film. For example, a circularly polarizing plate can be produced by combining the liquid crystal polymerized film having retardation of a ¼ wavelength with the polarizing plate.

Specific examples of the polarizing plate include an absorptive polarizing plate in which iodine or a dichroic dye is doped and a reflective polarizing plate such as a wire grid polarizing plate.

The highly functional polarizing plate of the invention has no alignment defects of the liquid crystal polymerized film, and therefore defects of an optical function can be reduced.

The highly functional polarizing plate is easily prepared, and therefore if the polymerizable liquid crystal composition of the invention is applied as the raw material of the liquid crystal polymer, the production cost of the highly functional polarizing plate is reduced.

In the highly functional polarizing plate of the invention, birefringence of the liquid crystal polymer is high, and therefore a thickness can be further reduced.

The liquid crystal polymerized film can be arranged inside the liquid crystal cell because of a small variation of retardation of the liquid crystal polymerized film by a heat history and small elution of impurities from the liquid crystal polymerized film to the liquid crystals.

The display device of the invention has no alignment defects of the liquid crystal polymerized film, and therefore generation of defects of the optical function can be reduced.

The steps of preparation of the embedded liquid crystal polymerized film are easy, and therefore the production cost of the liquid crystal polymerized film is decreased, and the production cost of the display device of the invention is decreased.

In the display device of the invention, birefringence of the embedded liquid crystal polymer is high, and therefore the thickness can be further reduced. The display device for a smartphone or the like requires thinness.

EXAMPLES

The invention is not limited only to Examples described below.

Unless otherwise specified by a particular temperature, Examples were performed at room temperature.

Definition of Terms

In Examples of the invention, "DCC" is 1,3-dicyclohexylcarbodiimide.

In Examples of the invention, "DMAP" is 4-dimethylaminopyridine.

In Examples of the invention, "IPA" is 2-propanol.

In Examples of the invention, "PGMEA" is propylene glycol monomethyl ether acetate.

In Examples of the invention, "MMP" is methyl 3-methoxypropionate.

In Examples of the invention, $T_{CN}$ is a transition temperature from a crystal phase to a nematic phase.

In Examples of the invention, $T_{NI}$ is a transition temperature from the nematic phase to an isotropic liquid.

In Examples of the invention, $T_{CI}$ is a transition temperature from the crystal phase to the isotropic liquid.

Procurement of Reagent

In Examples of the invention, "Irg-907" is Irgacure (trademark) 907 made by BASF Japan Ltd.

In Examples of the invention, "NCI-930" is Adeka Cruise (trademark) NCI-930 made by ADEKA Corporation.

In Examples of the invention, "FTX-218" is Futargent (trademark) FTX-218 made by Neos Co., Ltd.

In Examples of the invention, "TF370" is TEGOFlow (trademark) 370 of Evonik Japan, Inc.

In Examples of the invention, "polystyrene having a known molecular weight" is Lot No. 0006476 made by Tosoh Corporation.

In Examples of the invention, "palladium on carbon" is P1528 made by Tokyo Chemical Industry Co., Ltd.

In Examples of the invention, "polyimide substrate" is a substrate in which alignment film Lixon Aligner (registered trademark) PIA-5370 made by JNC CORPORATION is spin-coated to form a coating film, and a solvent is removed on a hot plate at 80° C., and then the coating film is calcinated in an oven at 230° C. for 30 minutes.

Equipment Used for Determination of Structure or the Like

In Examples of the invention, NMR was measured by using DRX-500 made by Bruker Corporation.

In Examples of the invention, a gel permeation chromatograph was measured by using LC-9A model made by Shimadzu Corporation.

In Examples of the invention, a column of the gel permeation chromatograph was Shodex (trademark) GF-7M HQ.

Equipment Used for Measuring Optical Characteristics or the Like

In Examples of the invention, a polarizing microscope was ECLIPSE E600POL made by Nikon Corporation.

In Examples of the invention, an ellipsometer was OPTIPRO Ellipsometer made by Shintech, Inc.

In Examples of the invention, the wire grid polarizing plate was UVT300A made by Polatechno Co., Ltd.

Equipment used for any Other Measurement

In Examples of the invention, a melting point apparatus was a system formed of temperature controller FP90 and hot stage FP82 by Mettler-Toledo K.K.

In Examples of the invention, a step between portions of the liquid crystal polymerized film was measured by using Alpha-Step IQ made by KLA-Tencor Corporation.

Apparatus Used for Preparation

In Examples of the invention, an ultra-high pressure mercury lamp was Multilight USH-250BY made by Ushio Inc.

In Examples of the invention, an ultraviolet intensity meter was UIT-150-A made by Ushio Inc.

In Examples of the invention, a photo detector for measuring illuminance of light at a wavelength in the vicinity of 313 nm was UVD-S313 made by Ushio Inc.

In Examples of the invention, a photo detector for measuring illuminance of light at a wavelength in the vicinity of 365 nm was UVD-S365 made by Ushio Inc.

Determination of Structure or the Like

A structure of a compound was determined by dissolving a compound being a measurement object in $CDCl_3$, and measuring $^1$H-NMR of the solution at 500 MHz. An actual measured value of NMR was expressed in teams of a value of a shift based on TMS, excluding ppm as a unit. In the expression of the actual measured value of NMR, s, d, t and m stand for a singlet, a doublet, a triplet and a multiplet, respectively.

Measurement of Weight Average Molecular Weight

A weight average molecular weight was determined by a gel permeation chromatograph. A temperature of a column during the development was set to 40° C. THF was used as a developing solvent for the gel permeation chromatograph. On the above occasion, polystyrene having a known molecular weight was used as a reference material for determining the weight average molecular weight.

Measurement of Optical Characteristics or the Like

Measurement of Transition Temperature of Compound

A transition temperature was measured by placing a sample on a hot stage in a melting point apparatus, and observing the sample with a polarizing microscope while a temperature was raised at a rate of 3° C. per minute.

Discrimination of Existence or Non-Existence of Alignment Defects

Existence or non-existence of alignment defects was judged by interposing a substrate-embedded liquid crystal polymerized film between two polarizing plates arranged in a crossed Nicol state. The substrate was rotated within a horizontal plane to visually confirm a light-dark state. A case when a place in which light was transmitted therethrough and seen was observed in a dark state or neither a light state nor a dark state was able to be confirmed was taken as "existence" of alignment defects. A case other than "existence of alignment defects was taken as "non-existence" of alignment defects."

Measurement of Retardation

Retardation of the liquid crystal polymerized film was measured by adjusting an angle of incident light to 0° by using the ellipsometer. A wavelength of light used for measuring the retardation was 550 nm.

Judgment of Homogeneous Alignment

Retardation was measured by changing an angle of incident light to a surface of the liquid crystal polymerized film from −50° to 50° at an increment of 5° by using the ellipsometer. Here, a direction of inclination of the angle of incident light is identical with a direction of a phase lagging axis of the liquid crystal polymerized film. A case where the following both conditions were satisfied was deemed that the liquid crystal polymerized film was in homogeneous alignment.

(a) A case where retardation to an incidence angle of the liquid crystal polymerized film was convex upward, and (b) a case where a difference between measured values of Re when an absolute value of each incidence angle was identical was within 5%.

Measurement of Film Thickness

A film thickness of the liquid crystal polymer having the glass substrate was measured according to the following procedures:

(1) a liquid crystal polymer was shaved off from a glass substrate having the liquid crystal polymer;

(2) a step between a portion having the liquid crystal polymer and a portion having no liquid crystal polymer was measured; and (3) the resulting measured value was taken as a film thickness.

Calculation of Birefringence

Birefringence of the liquid crystal polymer was calculated according to a formula: "(retardation)/(film thickness of liquid crystal polymer)."

Measurement of $T_{NI}$ of Polymerizable Liquid Crystal Composition $T_{NI}$ of the polymerizable liquid crystal composition was measured according to the procedures described below.

(1) A polymerizable liquid crystal composition solution was spin-coated onto a polyimide substrate at room temperature to prepare a coating film.

(2) A substrate having the coating film was left to stand on a hot plate at 80° C. for 3 minutes to remove a solvent from the coating film.

(3) The substrate having the coating film was left to stand for 3 minutes at room temperature under a nitrogen atmosphere to prepare the coating film of the polymerizable liquid crystal composition.

(4) $T_{NI}$ of the polymerizable liquid crystal composition was measured by placing the coating film of the polymerizable liquid crystal composition on a hot stage in a melting point apparatus, and observing the film with a polarizing microscope while a temperature was raised at a rate of 3° C. per minute.

Measurement of Lifetime of Liquid Crystal Phase

A liquid-crystal-phase's lifetime was measured according to the procedures described below.

(1) A polymerizable liquid crystal composition solution was spin-coated onto a polyimide substrate at room temperature to prepare a coating film.

(2) A substrate having the coating film was left to stand on a hot plate at 80° C. for 3 minutes to remove a solvent from the coating film.

(3) The substrate having the coating film was left to stand for 3 minutes under an atmosphere at room temperature to prepare a coating film of a polymerizable liquid crystal composition.

(4) The coating film of the polymerizable liquid crystal composition was left to stand at room temperature under an atmosphere, a time until precipitation of crystals from the polymerizable liquid crystal composition was able to be confirmed was measured by visual observation, and taken as the liquid-crystal-phase's lifetime.

However, when no crystal was precipitated from the polymerizable liquid crystal composition for 24 hours or more in measurement of the liquid-crystal-phase's lifetime, the liquid-crystal-phase's lifetime was taken as "24 hours or more." Moreover, when the coating film of the polymerizable liquid crystal composition was not formed into the liquid crystal phase at a time point of the procedure (3) for measuring the liquid-crystal-phase's lifetime in measuring the liquid-crystal-phase's lifetime, the lifetime was taken as "0."

Sample Preparation

Preparation of Photo-Alignment Agent

A polymer represented by formula (J) was synthesized in a manner similar to the method in Example 9 in JP 2012-087286 A.

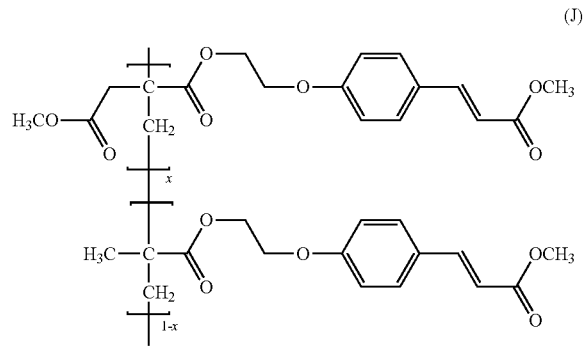

In formula (J), x was 0.1, and a weight average molecular weight was 53,700. Then, 5 parts by weight of the polymer represented by formula (J) was dissolved into 95 parts by weight of cyclopentanone, and a material obtained by filtration using a filter was named as photo-alignment agent (1).

Preparation of Photo-Alignment Film

A glass substrate with an alignment film was prepared according to the following procedures:

Procedure (1): Photo-alignment agent (1) was spin-coated onto glass to prepare a coating film.

Procedure (2): A substrate having the coating film was left to stand on a hot plate at 100° C. for 60 seconds to remove a solvent from the coating film.

Procedure (3): The coating film on the substrate was irradiated with linearly polarized ultraviolet light having predetermined power at room temperature from a direction of 90° relative to the coating film to prepare a glass substrate with an alignment film.

In the procedure, the linearly polarized ultraviolet light in procedure (3) was obtained by transmitting light from the ultra-high pressure mercury lamp through a wire grid polarizing plate. Moreover, an irradiation time in procedure (3) was adjusted by using a photo detector for measuring illuminance of light at a wavelength in the vicinity of 313 nm so as to be 200 mJ/cm$^2$ of exposure of the linearly polarized ultraviolet light on a surface of the coating film on the substrate in the Procedure (3). The irradiation time was 20 seconds to 40 seconds.

Compound (1-1-1-1) was synthesized according to the procedures described below.

stirred at −70° C. for 4 hours. The resulting reaction liquid was returned to room temperature, and then poured into ice water, and a deposit precipitate was filtered off. Crystals was well washed with water, and dried under reduced pressure. The residue was recrystallized in a mixture of ethyl acetate and heptane (v/v=5/1) to obtain 5.1 g of compound (ex-1).

Compound (ex-2) was synthesized according to a procedure similar to the method described in Example 1 in JP 2002-97170 A.

Then, 5.1 g of compound (ex-1), 16.8 g of compound (ex-2) and 1.6 g of MVP were added to 170 mL of dichloromethane, and the resulting mixture was stirred, under a nitrogen atmosphere, while the resulting mixture was cooled down to 5° C. by using an ice bath. Then, 27 mL of dichloromethane solution in which 13.8 g of DCC was dissolved was added dropwise thereto. After dropwise addition, the resulting mixture was stirred at room temperature for 16 hours. A deposit precipitated was filtered off, and an organic layer was washed with water and dried over anhydrous magnesium sulfate. Dichloromethane was distilled off under reduced pressure, and the residue was purified by column chromatography and recrystallized in a mixture of ethyl acetate and methanol (v/v=5/1) to obtain 17.3 g of compound (1-1-1-1). Here, a packing material in the column chromatography was silica gel. Here, an eluent was a mixture of toluene and ethyl acetate (v/v=9/1).

In compound (1-1-1-1), $T_{CN}$ was 87° C., and $T_{NI}$ was 126° C.

A signal of $^1$H-NMR in compound (1-1-1-1) is as described below.

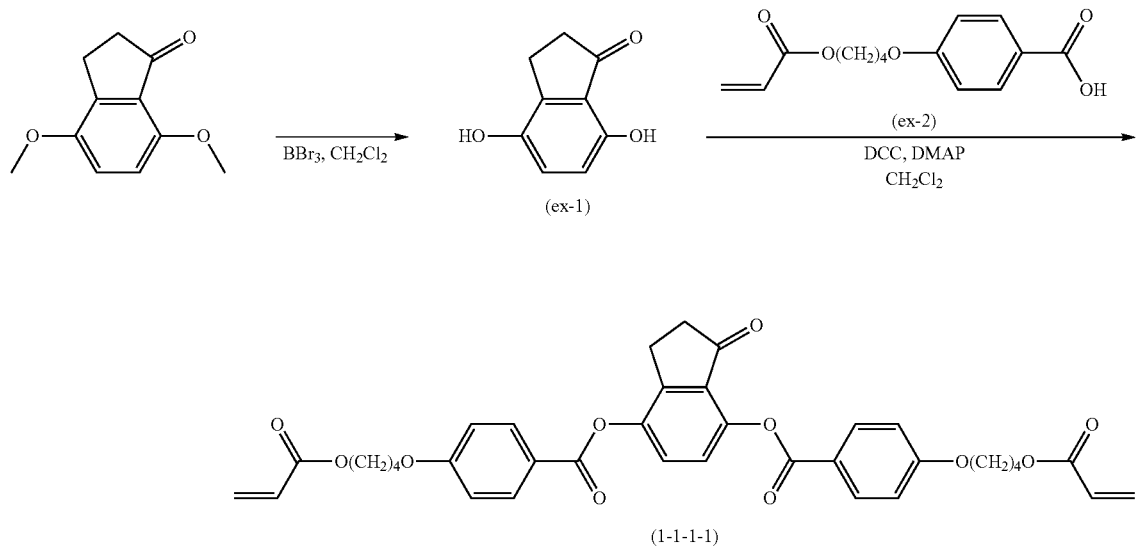

Then, 8.0 g of 4,7-dimethoxy-1-indanone was added to 80 mL of dichloromethane, and the resulting mixture was stirred, under a nitrogen atmosphere, while the resulting mixture was cooled down to −70° C. by using a dry ice bath. Then, 22.9 g of boron tribromide was added dropwise thereto. After dropwise addition, the resulting mixture was 8.19 (d, 2H), 8.17 (d, 2H), 7.49 (d, 1H), 7.23 (d, 1H), 7.00 (d, 2H), 6.99 (d, 2H), 6.44 (d, 2H), 6.18-6.10 (m, 2H), 5.85 (d, 2H), 4.29-4.25 (m, 4H), 4.14-4.08 (m, 4H), 3.08-3.05 (m, 2H), 2.70-2.65 (m, 2H), 1.98-1.88 (m, 8H).

Compound (1-1-13-1) was synthesized according to the procedures described below.

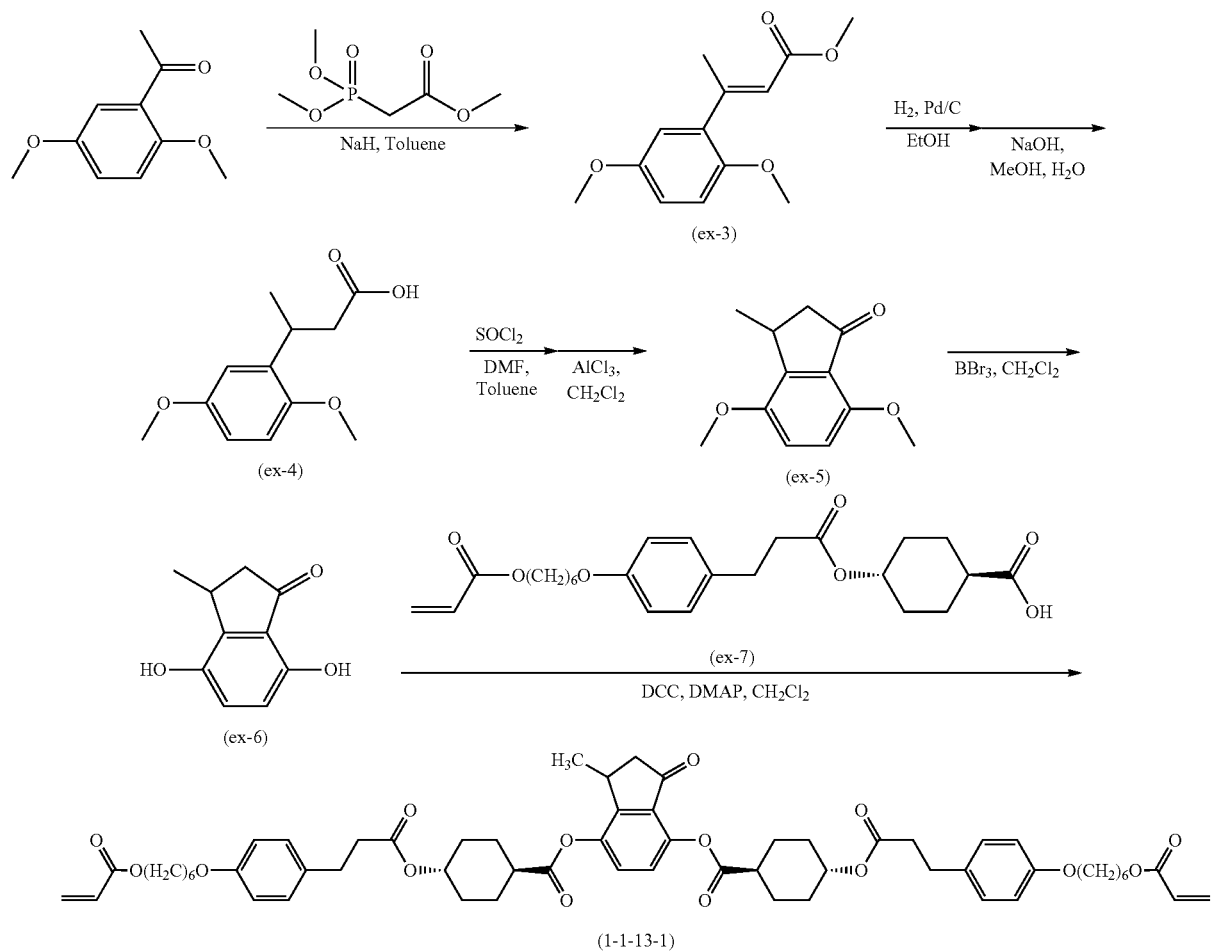

Then, 5.5 g of 60 wt % sodium hydride was added to 150 mL of toluene, and the resulting mixture was stirred at room temperature under a nitrogen atmosphere. Then, 25.0 g of trimethyl phosphonoacetate was added dropwise thereto, and the resulting mixture was stirred at room temperature for 1 hour. Then, 40 mL of toluene solution in which 19.0 g of 2',5'-dimethoxyacetophenone was dissolved was added dropwise to a liquid obtained, and the resulting mixture was stirred for 8 hours under heating reflux. Next, a saturated aqueous solution of ammonium chloride was added to a solution obtained, and an organic layer was obtained by extraction. The organic layer was washed with water, and dried over anhydrous magnesium sulfate. A solvent of a material obtained was distilled off under reduced pressure, and the resulting material was dried under reduced pressure to obtain 17.3 g of compound (ex-3).

Then, 17.3 g of compound (ex-3) and 1.2 g of palladium on carbon were added to 300 mL of ethanol, and the resulting mixture was stirred by using an autoclave at room temperature under a hydrogen atmosphere under 7 MPa for 24 hours. Liquid obtained was allowed to pass through Celite, and then a solvent was removed under reduced pressure to obtain the residue. Then, 4.9 g of sodium hydroxide, 72 mL of water and 72 mL of methanol were added to the residue obtained, and the resulting mixture was stirred under heating reflux for 3 hours, and then 3 N aqueous hydrochloric acid solution was added thereto, the resulting reaction liquid was acidified, toluene was added thereto, and an organic layer was obtained by extraction. The organic layer was washed with water, and dried over anhydrous magnesium sulfate. A solvent of a material obtained was distilled off under reduced pressure, and the residue was recrystallized in heptane to obtain 14.8 g of compound (ex-4).

Then, 14.8 g of compound (ex-4) and 0.1 g of DMF was added to 100 mL of toluene, and the resulting mixture was stirred at 60° C. under a nitrogen atmosphere. Then, 9.4 g of thionyl chloride was added dropwise thereto, and the resulting mixture was stirred at 60° C. for 4 hours. Then, a solvent of a liquid obtained under reduced pressure was removed to obtain the residue. Then, 9.2 g of aluminum chloride was added to 180 mL of dichloromethane, and the resulting mixture was stirred, under a nitrogen atmosphere, while the resulting mixture was cooled down to 5° C. by using an ice bath. Then, 50 mL of dichloromethane solution in which the residue was dissolved was added dropwise thereto. After dropwise addition, the resulting solution was stirred at room temperature for 24 hours. A liquid obtained was poured into ice water, and an organic layer was obtained by extraction. The organic layer was washed with a saturated aqueous solution of sodium hydrogencarbonate and then water, and dried over anhydrous magnesium sulfate. A solvent of a material obtained under reduced pressure was removed, the residue obtained was purified by column chromatography, and the resulting material was dried under reduced pressure to obtain 10.4 g of compound (ex-5). Here, a packing material in the column chromatography was silica gel, and an eluent was a mixture of toluene and ethyl acetate (v/v=3/1).

Then, 9.2 g of compound (ex-5) was added to 92 mL of dichloromethane, and the resulting mixture was stirred, under a nitrogen atmosphere, while the resulting mixture was cooled down to −70° C. by using a dry ice bath. Then, 24.5 g of boron tribromide was added dropwise thereto. After dropwise addition, the resulting mixture was stirred at −70° C. for 4 hours. A liquid obtained was returned to room temperature, and then poured into ice water, and filtered off to obtain a precipitate. Crystals of the precipitate was well washed with water, and dried under reduced pressure. The residue was recrystallized in a mixture of ethyl acetate and heptane (v/v=5/1) to obtain 7.9 g of compound (ex-6).

Compound (ex-7) was synthesized according to a procedure similar to the method described in Example 5 in JP 2016-047813 A.

Then, 1.9 g of compound (ex-6), 10.0 g of compound (ex-7) and 0.5 g of DMAP were added to 100 mL of dichloromethane, and the resulting mixture was stirred, under a nitrogen atmosphere, while the resulting mixture was cooled down to 5° C. by using an ice bath. Then, 10 mL of dichloromethane solution in which 4.9 g of DCC was dissolved was added dropwise thereto. After dropwise addition, the resulting mixture was stirred at room temperature for 16 hours. A deposit precipitated was filtered off, and an organic layer was washed with water and dried over anhydrous magnesium sulfate. Dichloromethane was distilled off under reduced pressure, and the residue was purified by column chromatography and recrystallized in a mixture of ethyl acetate and heptane (v/v=8/1) to obtain 6.4 g of compound (1-1-13-1). Here, a packing material in the column chromatography was silica gel. Here, an eluent was a mixture of toluene and ethyl acetate (v/v=9/1).

In compound (1-1-13-1), $T_{CN}$ was 68° C., and $T_{NI}$ was 130° C.

A signal of $^1$H-NMR in compound (1-1-13-1) is as described below.

7.29 (d, 1H), 7.11 (d, 4H), 6.99 (d, 1H), 6.81 (d, 4H), 6.41 (d, 2H), 6.16-6.08 (m, 2H), 5.82 (d, 2H), 4.81-4.73 (m, 2H), 4.17 (t, 4H), 3.93 (t, 4H), 3.44-3.38 (m, 1H), 2.95-2.87 (m, 5H), 2.68-2.55 (m, 6H), 2.30-2.17 (m, 5H), 2.11-2.04 (m, 4H), 1.82-1.67 (m, 12H), 1.54-1.39 (m, 12H), 1.34 (d, 3H).

Comparative Example 1

A structure of compound (C-1) is shown below. Compound (C-1) is a polymerizable liquid crystal compound.

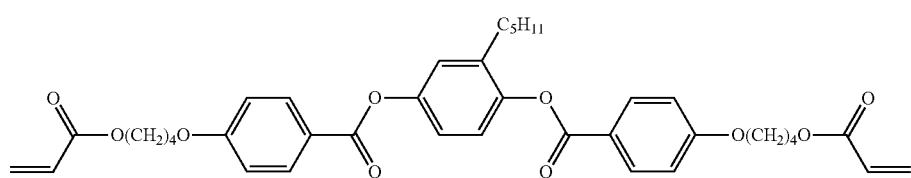

Compound (C-1) was synthesized according to the procedures described below.

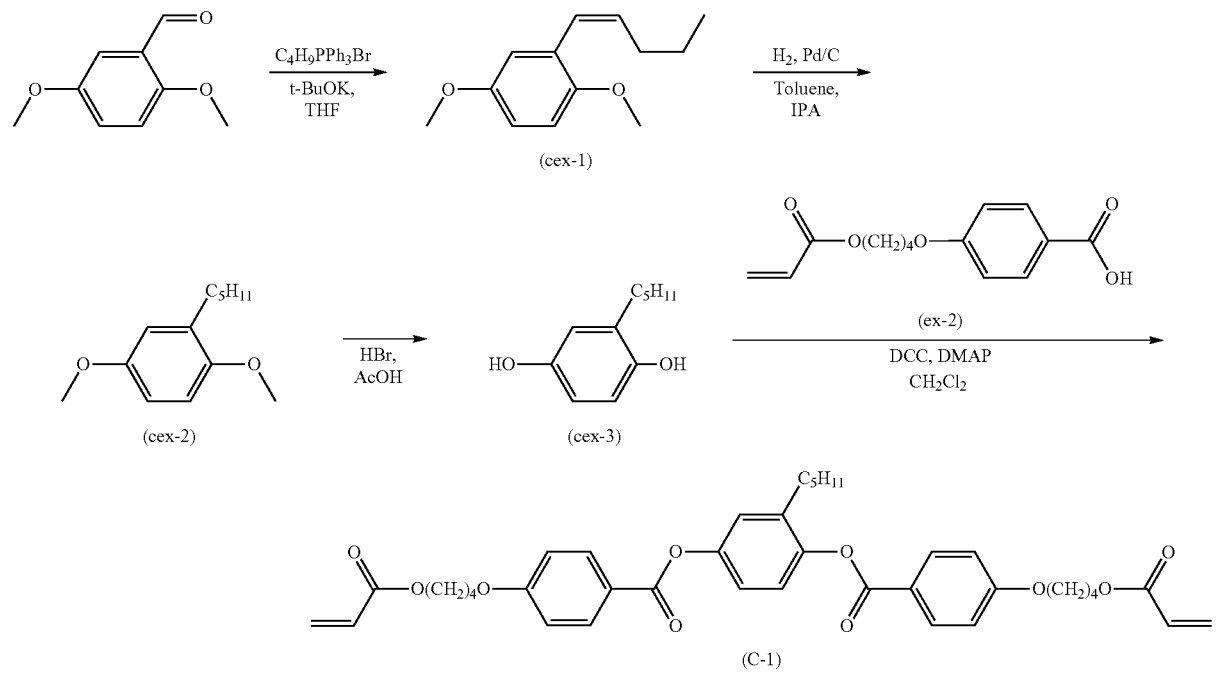

Then, 72.1 g of butyltriphenylphosphonium bromide was added to 700 mL of THF, and the resulting mixture was cooled at −30° C. and stirred under a nitrogen atmosphere by using a dry ice bath. Then, 20.3 g of t-butoxy potassium was added thereto. Next, 100 mL of THF solution in which 20 g of 2,5-dimethoxybenzaldehyde was dissolved was added dropwise thereto. After dropwise addition, the resulting mixture was stirred at −30° C. for 4 hours. The resulting reaction liquid was returned to room temperature, and then a saturated aqueous solution of ammonium chloride and toluene were added thereto, and an organic layer was obtained by extraction. The organic layer was washed with water, and dried over anhydrous magnesium sulfate. A solvent was distilled off under reduced pressure, the residue was purified by column chromatography, and the resulting material was dried under reduced pressure to obtain 15.9 g of compound (cex-1). Here, a packing material in the column chromatography was silica gel. Here, an eluent was a mixture of toluene and heptane (v/v=1/1).

Then, 15.9 g of compound (cex-1) and 1.6 g of palladium on carbon were added to a mixed solution of 130 mL of toluene and 130 mL of IPA, and the resulting mixture was stirred at room temperature for 24 hours under a hydrogen atmosphere under 7 MPa by using an autoclave. The resulting reaction liquid was passed through Celite, a solvent was distilled off under reduced pressure, the residue was purified by column chromatography, and the resulting material was dried under reduced pressure to obtain 15.7 g of compound (cex-2). Here, a packing material in the column chromatography was silica gel. Here, an eluent was a mixture of toluene and heptane (v/v=1/1).

Then, 15.7 g of compound (cex-2) and 63 mL of 48 wt % hydrobromic acid were added to 32 mL of acetic acid, and the resulting mixture was stirred for 16 hours while the resulting mixture was refluxed under a nitrogen atmosphere. Water and ethyl acetate were added thereto, an organic layer was obtained by extraction, and the organic layer was washed with water and dried over anhydrous magnesium sulfate. A solvent was distilled off under reduced pressure, and the residue was purified by column chromatography and recrystallized in a mixture of toluene and heptane (v/v=6/1) to obtain 11.3 g of compound (cex-3). Here, a packing material in the column chromatography was silica gel. Here, an eluent was a mixture of toluene and ethyl acetate (v/v=9/1).

Then, 11.3 g of compound (cex-3), 34.0 g of compound (ex-2) and 3.1 g of DMAP were added to 340 mL of dichloromethane, and the resulting mixture was stirred under a nitrogen atmosphere while the resulting mixture was cooled down to 5° C. by using an ice bath. Then, 56 mL of a dichloromethane solution in which 27.8 g of DCC was dissolved was added dropwise thereto. After dropwise addition, the resulting mixture was stirred at room temperature for 16 hours. An organic layer obtained by filtering off a deposit precipitated was washed with water, and dried over anhydrous magnesium sulfate. The residue obtained by removing dichloromethane under reduced pressure was purified by column chromatography, and recrystallized in an ethyl acetate-methanol mixture (v/v=4/1) to obtain 35.3 g of compound (C-1). Here, a packing material in the column chromatography was silica gel. Here, an eluent was a toluene-ethyl acetate mixture (v/v=9/1).

In compound (C-1), $T_{CN}$ was 34° C., and $T_{NI}$ was 43° C.

Comparative Example 2

A structure of compound (C-2) is shown below. Compound (C-2) is a polymerizable liquid crystal compound.

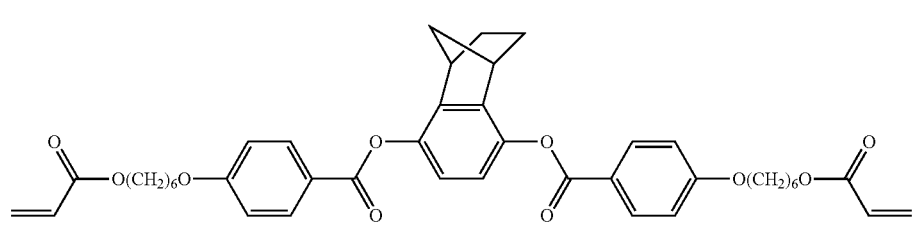

(C-2)

Compound (C-2) was synthesized in a manner similar to the method in Example 2 in JP 2010-241791 A.

$T_{CI}$ in compound (C-2) was 77° C. Compound (C-2) was a compound having no liquid crystal phase.

Comparative Example 3

A structure of compound (M2-1-1) is shown below. Compound (M2-1-1) is a polymerizable liquid crystal compound.

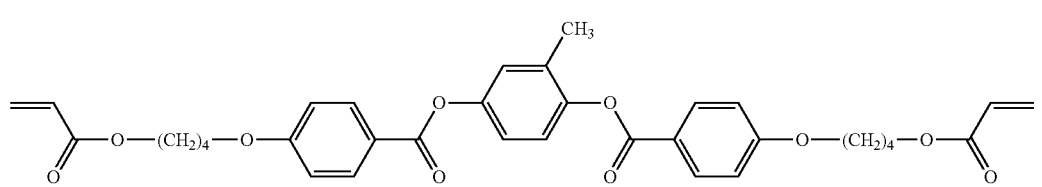

(M2-1-1)

Compound (M2-1-1) was synthesized according to the method described in Makromolekulare Chemie (1991), 192 (1), 59-74.

Table 1 summarizes a phase transition temperature and so forth of compound (1-1-1-1), compound (1-1-13-1), compound (C-1) and compound (C-2). A symbol "-" in Table 1 shows no development of any liquid crystal phase. A blank column in Table 1 shows absence of data corresponding thereto. A nematic phase is one form of a liquid crystal phase. Compound (1-1-1-1) and compound (1-1-13-1) each are compound, (1) in the invention. In compound (1-1-1-1) and compound (1-1-13-1) the nematic phase was developed. Compound (C-1), compound (C-2) and compound (M2-1-1) each are a comparative example.

TABLE 1

| Compound | Developed liquid crystal phase | $T_{CN}$ | $T_{NI}$ | Temperature range in which a liquid crystal phase is formed in the range of 60° C. to 120° C. |
|---|---|---|---|---|
| Compound (1-1-1-1) | Nematic phase | 87° C. | 126° C. | 33 K |
| Compound (1-1-13-1) | Nematic phase | 68° C. | 130° C. | 52 K |
| Compound (C-1) | Nematic phase | 34° C. | 43° C. | 0 K |
| Compound (C-2) | — | | | 0 K |
| Compound (M2-1-1) | Nematic phase | 78° C. | 119° C. | 41 K |

Table 1 shows that, in comparison with a conventional compound, compound (1-1-1-1) and compound (1-1-13-1) have a wider temperature range in which a liquid crystal phase is farmed in the range of 60° C. to 120° C.

Then, 70 parts by weight of a solvent were mixed with 30 parts by weight of compound (1-1-1-1), the resulting mixture was left to stand at 40° C. for 30 minutes in placing a mixture-containing container in warm water, and existence or non-existence of an insoluble residue of compound (1-1-1-1) was visually confirmed. A case where compound (1-1-13-1), compound (C-1) and compound (C-2) each were used in place of compound (1-1-1-1) was also confirmed. Table 2 shows results of existence or non-existence of the insoluble residue. In Table 2, "Good" means complete dissolution after being left to stand in the water bath. In Table 2, "poor" means existence of an insoluble matter after being left to stand in placing the mixture-containing container in warm water. Cyclohexanone, PGMEA and MMP each were tried as the solvent.

TABLE 2

| | Name of solvent | | |
|---|---|---|---|
| Name of compound | Cyclohexanone | PGMEA | MMP |
| Compound (1-1-1-1) | Good | Good | Good |
| Compound (1-1-13-1) | Good | Good | Good |
| Compound (C-1) | Good | Good | Good |
| Compound (C-2) | Good | Good | Good |
| Compound (M2-1-1) | Good | Poor | Poor |

Solubility of compound (1-1-1-1) and compound (1-1-13-1) in a solvent was found to be equivalent to solubility of compound (C-1) and compound (C-2), and superior to compound (M2-1-1).

Preparation of Polymerizable Liquid Crystal Composition

Compound (M2-1-2) was synthesized in a manner similar to a method described in Example 6 in JP 4063873 B.

Compound (M2-6-1) was synthesized by using 2,7-dihydroxy-9-methylfluorene in place of 2,7-dihydroxyfluorene in a procedure in Example 3 in JP 2003-238491 A.

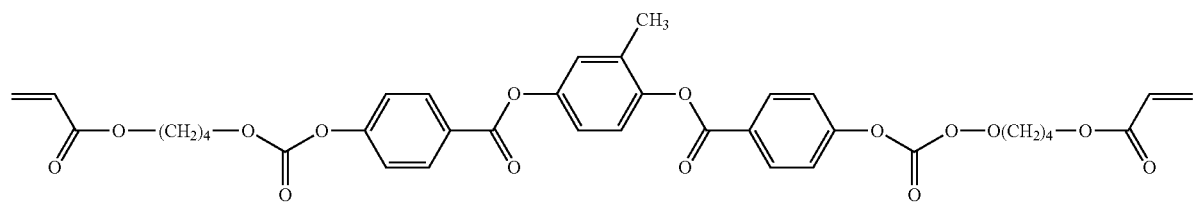

(M2-1-2)

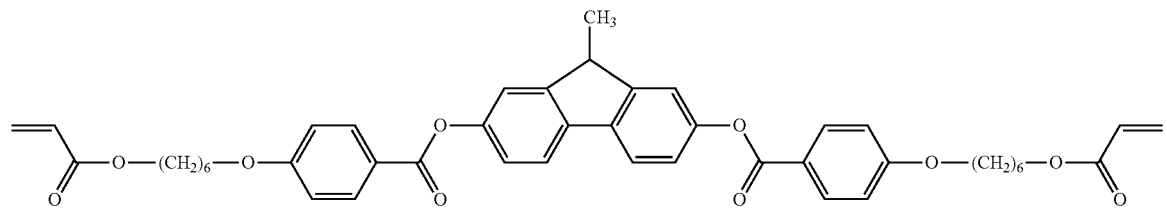

(M2-6-1)

Preparation of Polymerizable Liquid Crystal Composition

Example 1

Polymerizable liquid crystal compositions (S-1) to (S-4) each were prepared by mixing a compound described in Table 3 by an amount described in Table 3. A numeral 0 in Table 1 shows that a compound corresponding thereto was not mixed.

Polymerizable liquid crystal compositions (S-1) to (S-4) contain compound (1), and fall within the invention.

TABLE 3

| Name of polymerizable liquid crystal composition | Content and name of compound (1) | Content of compound (M2-1-1) | Content of compound (M2-1-2) | Content of compound (M2-6-1) | Content and name of polymerization initiator | Content and name of surfactant |
|---|---|---|---|---|---|---|
| Polymerizable liquid crystal composition (S-1) | 94.08% by weight of compound (1-1-1-1) | 0 | 0 | 0 | 5.64% by weight of Irg-907 | 0.28% by weight of FTX-218 |
| Polymerizable liquid crystal composition (S-2) | 46.22% by weight of compound (1-1-1-1) | 46.21% by weight | 0 | 0 | 7.39% by weight of NCI-930 | 0.18% by weight of FTX-218 |
| Polymerizable liquid crystal composition (S-3) | 36.20% by weight of compound (1-1-1-1) | 0 | 36.20% by weight | 18.10% by weight | 9.05% by weight of Irg-907 | 0.45% by weight of TF370 |
| Polymerizable liquid crystal composition (S-4) | 47.44% by weight of compound (1-1-13-1) | 37.95% by weight | 0 | 9.49% by weight | 4.74% by weight of NCI-930 | 0.38% by weight of TF370 |

Comparative Example 4

Polymerizable liquid crystal compositions (SC-1) to (SC-4) each were prepared by mixing a compound described in Table 4 by an amount described in Table 4. A numeral "0" in Table 4 shows that a compound corresponding thereto was not mixed.

Polymerizable liquid crystal compositions (SC-1) to (SC-4) contain no compound (1), and do not fall within the invention.

TABLE 4

| Name of polymerizable liquid crystal composition | Content of compound (C-1) | Content of compound (C-2) | Content of compound (M2-1-1) | Content and name of polymerization initiator | Content and name of surfactant |
|---|---|---|---|---|---|
| Polymerizable liquid crystal composition (SC-1) | 94.08% by weight | 0 | 0 | 5.64% by weight of Irg-907 | 0.28% by weight of FTX-218 |
| Polymerizable liquid crystal composition (SC-2) | 0 | 94.08% by weight | 0 | 5.64% by weight of Irg-907 | 0.28% by weight of FTX-218 |
| Polymerizable liquid crystal composition (SC-3) | 0 | 0 | 94.08% by weight | 5.64% by weight of Irg-907 | 0.28% by weight of FTX-218 |
| Polymerizable liquid crystal composition (SC-4) | 46.22% by weight | 0 | 46.21% by weight | 7.39% by weight of NCI-930 | 0.18% by weight of FTX-218 |

Preparation of Polymerizable Liquid Crystal Composition Solution

Example 2

A mixed solution of polymerizable liquid crystal compositions (S-1) to (S-4) each and a solvent was prepared to prepare polymerizable liquid crystal composition solutions (T-1) to (T-5). Then, a numeral 0 in Table 5 shows that a solvent corresponding thereto was not mixed.

Polymerizable liquid crystal composition solutions (T-1) to (T-5) contain compound (1), and fall within the invention.

TABLE 5

| Name of polymerizable liquid crystal composition solution | Content and name of polymerizable liquid crystal composition | Content and name of first solvent | Content and name of second solvent |
|---|---|---|---|
| Polymerizable liquid crystal composition solution (T-1) | 22% by weight of polymerizable liquid crystal composition (S-1) | 78% by weight of cyclohexanone | 0 |

TABLE 5-continued

| Name of polymerizable liquid crystal composition solution | Content and name of polymerizable liquid crystal composition | Content and name of first solvent | Content and name of second solvent |
|---|---|---|---|
| Polymerizable liquid crystal composition solution (T-2) | 22% by weight of polymerizable liquid crystal composition (S-2) | 78% by weight of cyclohexanone | 0 |
| Polymerizable liquid crystal composition solution (T-3) | 20% by weight of polymerizable liquid crystal composition (S-3) | 80% by weight of PGMEA | 0 |
| Polymerizable liquid crystal composition solution (T-4) | 30% by weight of polymerizable liquid crystal composition (S-3) | 70% by weight of MMP | 0 |
| Polymerizable liquid crystal composition solution (T-5) | 20% by weight of polymerizable liquid crystal composition (S-4) | 24% by weight of cyclohexanone | 56% by weight of PGMEA |

Comparative Example 5

A mixed solution of polymerizable liquid crystal compositions (SC-1) to (SC-4) each and a solvent was prepared to prepare polymerizable liquid crystal composition solutions (TC-1) to (TC-4).

Polymerizable liquid crystal composition solutions (TC-1) to (TC-4) contain no compound (1), and do not fall within the invention.

TABLE 6

| Name of polymerizable liquid crystal composition solution | Content and name of polymerizable liquid crystal composition | Content and name of solvent |
|---|---|---|
| Polymerizable liquid crystal composition solution (TC-1) | 22% by weight of a polymerizable liquid crystal composition (SC-1) | 78% by weight of cyclohexanone |
| Polymerizable liquid crystal composition solution (TC-2) | 22% by weight of a polymerizable liquid crystal composition (SC-2) | 78% by weight of cyclohexanone |
| Polymerizable liquid crystal composition solution (TC-3) | 22% by weight of a polymerizable liquid crystal composition (SC-3) | 78% by weight of cyclohexanone |
| Polymerizable liquid crystal composition solution (TC-4) | 22% by weight of a polymerizable liquid crystal composition (SC-4) | 78% by weight of cyclohexanone |

Example 3

A substrate on which a polymerizable liquid crystal composition was applied was prepared according to the following procedures:

Procedure (1): A polymerizable liquid crystal composition solution was spin-coated onto a polyimide substrate;

procedure (2): the polyimide substrate was left to stand on a hot plate at 80° C. for 3 minutes; and procedure (3): the polyimide substrate was left to stand under a nitrogen atmosphere for 3 minutes to obtain the substrate on which the polymerizable liquid crystal composition was applied.

Table 7 shows physical properties of polymerizable liquid crystal compositions (S-1) to (S-4) and polymerizable liquid crystal compositions (SC-1) to (SC-4). Polymerizable liquid crystal compositions (S-1) to (S-4) contain compound (1).

Then, a symbol "–" of $T_{NI}$ in Table 7 shows the polymerizable liquid crystal composition had no liquid crystal phase, and therefore $T_{NI}$ was unable to be measured. After procedure 3 in Example 3, the polymerizable liquid crystal composition on the polyimide substrate was confirmed to hold a liquid crystal phase at room temperature in the case of polymerizable liquid crystal composition (S-1) to polymerizable liquid crystal composition (S-4), polymerizable liquid crystal composition (SC-1), polymerizable liquid crystal composition (SC-3) and polymerizable liquid crystal composition (SC-4).

TABLE 7

| Name of polymerizable liquid crystal composition | $T_{NI}$ | Lifetime of liquid crystal phase |
|---|---|---|
| Polymerizable liquid crystal composition (S-1) | 115° C. | 24 hours or more |
| Polymerizable liquid crystal composition (S-2) | 110° C. | 8 hours |
| Polymerizable liquid crystal composition (S-3) | 118° C. | 8 hours |
| Polymerizable liquid crystal composition (S-4) | 126° C. | 10 hours |
| Polymerizable liquid crystal composition (SC-1) | 32° C. | 24 hours or more |
| Polymerizable liquid crystal composition (SC-2) | — | 0 |
| Polymerizable liquid crystal composition (SC-3) | 103° C. | 5 minutes |
| Polymerizable liquid crystal composition (SC-4) | 78° C. | 2 hours |

Polymerizable liquid crystal compositions (S-1) to (S-4) contain compound (1). Polymerizable liquid crystal compositions (S-1) to (S-4) were found to have a wide temperature range of developing a liquid crystal phase and to be excellent in long-term stability of the liquid crystal phase.

Preparation of Substrate-Embedded Liquid Crystal Polymerized Film

Example 4

A substrate-embedded liquid crystal polymerized film was prepared according to the following procedures:

Procedure (1): A polymerizable liquid crystal composition solution was applied onto a glass substrate with an alignment film subjected to polarized ultraviolet light treatment by spin coating;

procedure (2): the substrate was left to stand on a hot plate at 80° C. for 3 minutes;

procedure (3): subsequently, the substrate was left to stand at room temperature for 3 minutes; and procedure (4): the polymerizable liquid crystal composition on the substrate was irradiated with light having predetermined power from an ultra-high pressure mercury lamp at room temperature under a nitrogen atmosphere from a direction of 90° relative thereto to cause polymerization of the polymerizable liquid crystal composition on the substrate.

In the procedure, an irradiation time in procedure (4) was adjusted in the range from 5 seconds to 40 seconds by using a photo detector for measuring illuminance of light at a wavelength in the vicinity of 365 nm so as to be 500 mJ/cm² in exposure of light of the ultra-high pressure mercury lamp on a surface of the polymerizable liquid crystal composition in the procedure (4).

Example 5

Table 8 describes physical properties of a substrate-embedded liquid crystal polymerized film. In a name of the polymerizable liquid crystal composition solution, a raw material of the liquid crystal polymer of the substrate-embedded liquid crystal polymerized film in Table 8 is shown. Then, a symbol "-" in Table 8 show that no measurement was performed.

TABLE 8

| Name of polymerizable liquid crystal composition solution | Judgment of homogeneous alignment | Alignment defects | Retardation/ nm | Birefringence |
|---|---|---|---|---|
| Polymerizable liquid crystal composition solution (T-1) | Homogeneous alignment | No | 142 | 0.17 |
| Polymerizable liquid crystal composition solution (T-2) | Homogeneous alignment | No | 152 | 0.16 |
| Polymerizable liquid crystal composition solution (T-3) | Homogeneous alignment | No | 255 | 0.18 |
| Polymerizable liquid crystal composition solution (T-4) | Homogeneous alignment | No | 138 | 0.19 |
| Polymerizable liquid crystal composition solution (T-5) | Homogeneous alignment | No | 135 | 0.15 |
| Polymerizable liquid crystal composition solution (TC-1) | No homogeneous alignment | Yes | — | — |
| Polymerizable liquid crystal composition solution (TC-2) | No homogeneous alignment | Yes | — | — |
| Polymerizable liquid crystal composition solution (TC-3) | Homogeneous alignment | Existence | — | — |
| Polymerizable liquid crystal composition solution (TC-4) | Homogeneous alignment | No | 133 | 0.11 |

As the liquid crystal polymer prepared by using polymerizable liquid crystal composition solutions (T-1) to (T-5) as the raw material, the liquid crystal polymer having no precipitation of crystals from the polymerizable liquid crystal composition and no alignment defects was obtained.

In the liquid crystal polymer prepared by using polymerizable liquid crystal composition solutions (TC-1) and (TC-2) as the raw material, no homogeneous alignment was obtained. The liquid crystal polymer prepared by using polymerizable liquid crystal composition solution (TC-3) as the raw material had alignment defects.

As the liquid crystal polymer prepared by using polymerizable liquid crystal composition solution (TC-4) as the raw material, the liquid crystal polymer having no precipitation of crystals from the polymerizable liquid crystal composition and no alignment defects was obtained and formed into the liquid crystal polymer having small birefringence.

The birefringence of the substrate-embedded liquid crystal polymer prepared from polymerizable liquid crystal compositions (S-1) to (S-4) was significantly higher than the birefringence of the substrate-embedded liquid crystal polymer prepared from polymerizable liquid crystal composition (SC-4).

From the experimental results described above, the substrate-embedded liquid crystal polymer having no defects and having large birefringence is clearly shown to be obtained by using the polymerizable liquid crystal composition containing compound (1-1-1-1) or compound (1-1-13-1) as a part of the raw material.

From the experimental results described above, the liquid crystal polymerized film usable for a phase difference film, a polarizing plate or a display device is found to be free from alignment defects and be able to be thinned, while production cost is suppressed, by applying compound (1-1-1-1) or compound (1-1-13-1) as a part of the raw material of the polymerizable liquid crystal composition. Thus, the defects of an optical function of the phase difference film, the polarizing plate and the display device can be obviously reduced, and the phase difference film, the polarizing plate and the display device can be obviously thinned while material cost of the phase difference film, the polarizing plate and the display device is suppressed.

What is claimed is:
1. A polymerizable liquid crystal compound, represented by formula (1):

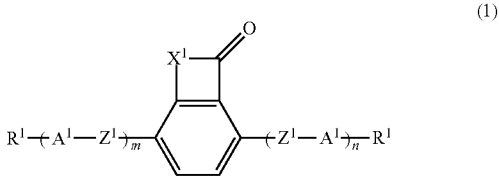

(1)

wherein, in formula (1),
A¹ is independently 1,4-phenylene, 1,4-cyclohexylene, 1,4-cyclohexenylene, pyridine-2,5-diyl, 1,3-dioxane-2,5-diyl or naphthalene-2,6-diyl, and in the 1,4-phenylene or naphthalene-2,6-diyl, at least one hydrogen may be replaced by fluorine, chlorine, trifluoromethyl, alkyl having 1 to 10 carbons, alkenyl having 2 to 10 carbons, alkoxy having 1 to 10 carbons, alkoxycarbonyl having 1 to 10 carbons, alkylester having 1 to 10 carbons, alkanoyl having 1 to 10 carbons or a polymerizable functional group,
Z¹ is independently a single bond, —OCH₂—, —CH₂O—, —COO—, —OCO—, —CF₂O—, —OCF₂—, —CH₂CH₂—, —CF₂CF₂—, —OCH₂CH₂O—, —CH=CHCOO—, —OCOCH=CH—, —CH₂CH₂COO—, —OCOCH₂CH₂—, —CH₂CH₂OCO—, —COOCH₂CH₂—, —CH=CH—, —N=C (CH₃)—, —C(CH₃)=N—, —N=N—, —C≡C— or —CH=N—N=CH—,
m and n are independently an integer from 0 to 5, in which an expression: 1≤m+n≤8 holds,
X¹ is alkylene having 1 to 5 carbons, and in the alkylene, at least one —CH₂— may be replaced by —CO—, —S—, —O— or —NH—, and at least one —CH$_2$—CH$_2$— may be replaced by —CH=CH—, at least one hydrogen in —CH$_2$—, —CH= or —NH— described above may be replaced by fluorine, chlorine, trifluoromethyl, alkyl having 1 to 10 carbons or alkanoyl having 1 to 10 carbons, one of R$^1$ is a polymerizable functional group, and the other of R$^1$ is a polymerizable functional group, fluorine, chlorine, trifluoromethyl, trifluoromethoxy, cyano, alkyl having 1 to 12 carbons, alkoxy having 1 to 12 carbons, alkenyl having 2 to 12 carbons, alkylester having 1 to 12 carbons or alkoxycarbonyl having 1 to 12 carbons.

2. The polymerizable liquid crystal compound according to claim 1, wherein the polymerizable functional group is independently represented by formula (2):

(2)

wherein, in formula (2),

Y$^1$ is a single bond, —O—, —COO—, —OCO— or —OCOO—, and

Q$^1$ is a single bond or alkylene having 1 to 20 carbons, and in the alkylene, at least one —CH$_2$— may be replaced by —O—, —COO— or —OCO—, and PG is a polymerizable group represented by any one of formula (PG-1) to formula (PG-9):

(PG-1)

(PG-2)

(PG-3)

(PG-4)

(PG-5)

(PG-6)

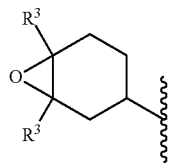
(PG-7)

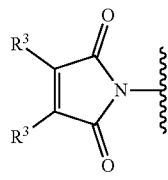
(PG-8)

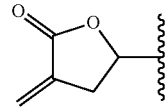
(PG-9)

wherein, in formula (PG-1) to formula (PG-9), R$^3$ is each independently hydrogen, fluorine, methyl, ethyl or trifluoromethyl.

3. The polymerizable liquid crystal compound according to claim 1, wherein Z$^1$ is independently a single bond, —OCH$_2$—, —CH$_2$O—, —COO—, —OCO—, —CH$_2$CH$_2$—, —CH=CHCOO—, —OCOCH=CH—, —CH$_2$CH$_2$COO— or —OCOCH$_2$CH$_2$—.

4. The polymerizable liquid crystal compound according to claim 2, wherein both of R$^1$ are a group represented by formula (2).

5. The polymerizable liquid crystal compound according to claim 1, wherein X$^1$ is alkylene having 2 to 4 carbons, and in the alkylene, —CH$_2$— may be replaced by —CO—, —S—, —O— or —NH—, and at least one hydrogen may be replaced by fluorine, chlorine, trifluoromethyl, alkyl having 1 to 5 carbons or alkanoyl having 1 to 5 carbons.

6. The polymerizable liquid crystal compound according to claim 2, wherein both of R$^1$ are a group represented by formula (2), and PG is a polymerizable group represented by formula (PG-1).

7. The polymerizable liquid crystal compound according to claim 1, wherein m and n are independently 1, 2 or 3.

8. A polymerizable liquid crystal composition, containing the polymerizable liquid crystal compound according to claim 1.

9. A polymerizable liquid crystal composition, containing 10 to 100% by weight of the polymerizable liquid crystal compound according to claim 1 based on the total weight of the polymerizable liquid crystal compound.

10. A liquid crystal polymerized film, wherein the polymerizable liquid crystal composition according to claim 8 is polymerized.

11. A liquid crystal polymerized film comprising a substrate-embedded liquid crystal polymer, and the liquid crystal polymerized film having an alignment film on a substrate, wherein a polymerizable liquid crystal compound in the polymerizable liquid crystal composition according to claim 8 is aligned by the alignment film and polymerized.

12. The liquid crystal polymerized film according to claim 11, wherein the polymerizable liquid crystal compound in the polymerizable liquid crystal composition is immobilized in a state of homogeneous alignment.

13. A phase difference film comprising the liquid crystal polymerized film according to claim 10.

14. A polarizing plate having the liquid crystal polymerized film according to claim 10.

15. A display device having the liquid crystal polymerized film according to claim 10.

* * * * *

UNITED STATES PATENT AND TRADEMARK OFFICE
CERTIFICATE OF CORRECTION

PATENT NO. : 10,844,283 B2
APPLICATION NO. : 15/896019
DATED : November 24, 2020
INVENTOR(S) : Daisuke Ootsuki Page 1 of 2

It is certified that error appears in the above-identified patent and that said Letters Patent is hereby corrected as shown below:

At Columns 54-55, Claim 1 should read as follows:
1. A polymerizable liquid crystal compound, represented by formula (1):

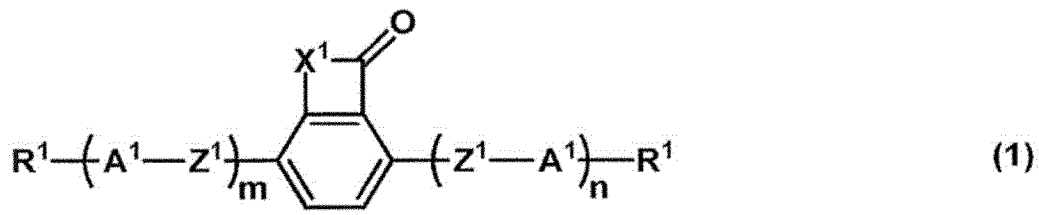

wherein, in formula (1),
$A^1$ is independently 1,4-phenylene, 1,4-cyclohexylene, 1,4-cyclohexenylene, pyridine-2,5-diyl, 1,3-dioxane-2,5-diyl or naphthalene-2,6-diyl, and in the 1,4-phenylene or naphthalene-2,6-diyl, at least one hydrogen may be replaced by fluorine, chlorine, trifluoromethyl, alkyl having 1 to 10 carbons, alkenyl having 2 to 10 carbons, alkoxy having 1 to 10 carbons, alkoxycarbonyl having 1 to 10 carbons, alkylester having 1 to 10 carbons, alkanoyl having 1 to 10 carbons or a polymerizable functional group,
$Z^1$ is independently a single bond, -OCH$_2$-, -CH$_2$O-, -COO-, -OCO-, -CF$_2$O-, -OCF$_2$-, -CH$_2$CH$_2$-, -CF$_2$CF$_2$-, -OCH$_2$CH$_2$O-, -CH=CHCOO-, -OCOCH=CH-, -CH$_2$CH$_2$COO-, -OCOCH$_2$CH$_2$-, -CH$_2$CH$_2$OCO-, -COOCH$_2$CH$_2$-, -CH=CH-, -N=CH-, -CH=N-, -N=C(CH$_3$)-, -C(CH$_3$)=N-, -N=N-, -C≡C- or -CH=N-N=CH-,
m and n are independently an integer from 0 to 5, in which an expression: $1 \leq m + n \leq 8$ holds,
$X^1$ is alkylene having 1 to 5 carbons, and in the alkylene, at least one -CH$_2$- may be replaced by -CO-, -S-, -O- or -NH-, and at least one -CH$_2$-CH$_2$- may be replaced by -CH=CH-, Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office* at least one hydrogen in -CH$_2$-, -CH= or -NH- described above may be replaced by fluorine, chlorine, trifluoromethyl, alkyl having 1 to 10 carbons or alkanoyl having 1 to 10 carbons, one of R$^1$ is a polymerizable functional group, and the other of R$^1$ is a polymerizable functional group, fluorine, chlorine, trifluoromethyl, trifluoromethoxy, cyano, alkyl having 1 to 12 carbons, alkoxy having 1 to 12 carbons, alkenyl having 2 to 12 carbons, alkylester having 1 to 12 carbons or alkoxycarbonyl having 1 to 12 carbons.